US009727774B2

(12) United States Patent
Brownlee

(10) Patent No.: US 9,727,774 B2
(45) Date of Patent: *Aug. 8, 2017

(54) SYSTEM AND METHOD FOR DETECTING AN ORGANIC BODY FOR AUTHENTICATION

(71) Applicant: Silk ID Systems, Inc., Santa Clara, CA (US)

(72) Inventor: Kenneth Brownlee, Palo Alto, CA (US)

(73) Assignee: SILK ID SYSTEMS, INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/218,862

(22) Filed: Jul. 25, 2016

(65) Prior Publication Data

US 2017/0098116 A1 Apr. 6, 2017

Related U.S. Application Data

(63) Continuation of application No. 14/873,729, filed on Oct. 2, 2015, now Pat. No. 9,400,916.

(51) Int. Cl.
*G06K 9/00* (2006.01)
*G01B 11/30* (2006.01)
*A61B 5/117* (2016.01)
*A61B 5/1172* (2016.01)

(52) U.S. Cl.
CPC ........ *G06K 9/00114* (2013.01); *A61B 5/1172* (2013.01); *G01B 11/303* (2013.01); *G06K 9/0008* (2013.01); *G06K 9/0012* (2013.01); *G06K 9/00046* (2013.01)

(58) Field of Classification Search
CPC ............. G06K 9/00114; G06K 9/0012; G06K 9/00046; A61B 5/1172
See application file for complete search history.

(56) References Cited

U.S. PATENT DOCUMENTS

| | | | |
|---|---|---|---|
| 9,400,916 B1 * | 7/2016 | Brownlee | ............ A61B 5/1172 |
| 2007/0211926 A1 | 9/2007 | Shinzaki | |
| 2010/0098302 A1 | 4/2010 | Shin | |
| 2013/0022248 A1 | 1/2013 | Rowe | |
| 2013/0070088 A1 | 3/2013 | Ito | |
| 2014/0153791 A1 | 6/2014 | Kim | |
| 2014/0270416 A1 | 9/2014 | Minteer | |
| 2015/0078633 A1 | 3/2015 | Hung | |
| 2016/0063300 A1 | 3/2016 | Du | |

OTHER PUBLICATIONS

International Search Report and Written Opinion mailed Sep. 15, 2016 in International Application PCT/US2016/039060.

* cited by examiner

*Primary Examiner* — WB Perkey
(74) *Attorney, Agent, or Firm* — Pillsbury Winthrop Shaw Pittman LLP

(57) ABSTRACT

Methods, systems, and programming for user identification and authentication are presented. In one example, an apparatus for user authentication is disclosed. The apparatus comprises: a surface on which an object is placed; a light source configured for providing light illuminating a first portion of the surface; a brightness measuring unit configured for measuring brightness distribution in a second portion of the surface, wherein the brightness distribution is caused by the object that spreads the light from the first portion to the second portion; and a determiner configured for determining whether the object is an organic body part based on the brightness distribution.

27 Claims, 21 Drawing Sheets

SYSTEM AND METHOD FOR DETECTING AN ORGANIC BODY FOR AUTHENTICATION

CROSS-REFERENCE TO RELATED APPLICATIONS

This non-provisional application is a continuation of U.S. patent application Ser. No. 14/873,729 filed Oct. 2, 2015, the contents of which are incorporated herein in its entirety.

BACKGROUND

1. Technical Field

The present disclosure relates to user authentication and identification; particularly, user authentication and identification based on an organic body detection.

2. Technical Background

Biometric systems have been widely used for user identification and authentication based on biometric information. A big challenge for a biometric system is detecting and rejecting a spoof attack, where a reproduction of a biometric sample is presented to the biometric system by an unauthorized person seeking to illicitly gain access to another user's account, data, or privileges. An example of a spoof attack is the presentation of a molded model or photograph of a fingerprint, instead of the rightful owner's true finger, to a biometric fingerprint reader. Most conventional biometric systems do not have an effective way to detect a spoof attack, which may be called organic body detection or spoof detection. This can cause a serious reliability and security issue of the biometric system.

Therefore, there is a need to provide a user identification/authentication solution with improved reliability.

SUMMARY

The present teaching relates to methods, systems, and programming for user authentication and identification. Particularly, the present teaching is directed to methods, systems, and programming for user authentication and identification based on organic body detection.

In one example, an apparatus for user authentication is disclosed. The apparatus comprises: a surface on which an object is placed; a light source configured for providing light illuminating a first portion of the surface; a brightness measuring unit configured for measuring brightness distribution in a second portion of the surface, wherein the brightness distribution is caused by the object that spreads the light from the first portion to the second portion; and a determiner configured for determining whether the object is an organic body part based on the brightness distribution.

In a different example, a method implemented on a device for determining whether an object is an organic body part is disclosed. Presence of an object is sensed when a person places an object on a surface of the device. Light is provided for illuminating a first portion of the surface. Brightness distribution in a second portion of the surface is measured. The brightness distribution is caused by the object that spreads the light from the first portion to the second portion. Whether the object is an organic body part is determined based on the brightness distribution.

In another example, a system for recognizing a person is disclosed. The system comprises: a surface on which an object is placed by the person; a light source configured for providing light illuminating a first portion of the surface; a brightness measuring unit configured for measuring brightness distribution in a second portion of the surface, wherein the brightness distribution is caused by the object that spreads the light from the first portion to the second portion; a spread-based determiner configured for determining whether the object is an organic body part based on the brightness distribution to generate a determination result; a biometric image processing unit configured for obtaining a biometric image of the object; and an identity determiner configured for recognizing the person based on the biometric image and the determination result.

In yet another example, an apparatus for reading biometric features of an object is disclosed. The apparatus comprises: a light source configured for providing light illuminating a first portion of the object, wherein the object is not in contact with the apparatus; a brightness measuring unit configured for measuring brightness distribution in a second portion of the object, wherein the brightness distribution is caused by the object that spreads the light from the first portion to the second portion; and a determiner configured for determining whether the object is an organic body part based on the brightness distribution.

Other concepts relate to software for implementing the present teaching on user authentication based on organic body detection. A software product, in accord with this concept, includes at least one machine-readable non-transitory medium and information carried by the medium. The information carried by the medium may be executable program code data, parameters in association with the executable program code, and/or information related to a user, a request, content, or information related to a social group, etc.

Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
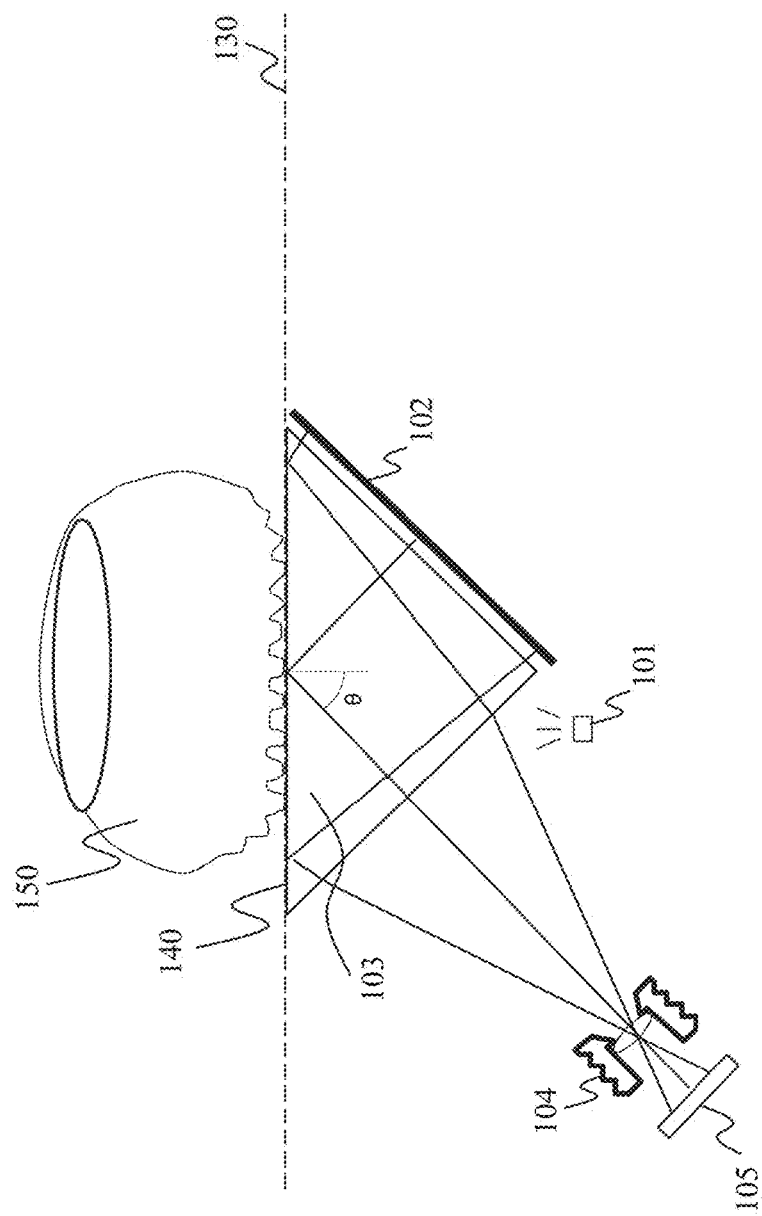
FIG. 1 illustrates a conventional fingerprint reader, according to prior art.

In the following detailed description, numerous specific details are set forth by way of examples in order to provide a thorough understanding of the relevant teachings. However, it should be apparent to those skilled in the art that the present teachings may be practiced without such details or in conjunction with additional features. In other instances, well known methods, procedures, systems, components, and/or circuitry have been described at a relatively high-level, without detail, in order to avoid unnecessarily obscuring aspects of the present teachings.

The present disclosure describes method, system, and programming aspects of detecting a spoof attack by determining whether an object is an organic body part.

According to one embodiment of the presenting teaching, an authentication apparatus comprises a transparent platen on which a finger is placed on by a person and a light source illuminating a first portion of the platen without directly illuminating a second portion of the platen. The finger may be or may be not in contact with both portions of the platen. The apparatus may also comprise an imaging system measuring the spread of light from the directly illuminated portion of the platen into parts of the finger touching the non-directly illuminated portion of the platen. Measurement and characterization of this spread of light can be compared to predetermined values to determine if the presented finger is genuine. This may be called a spoof detection about whether this is a spoof or fake finger. The apparatus may determine whether to authenticate the person based on the spoof detection and stored biometric data provided by the person. For example, the apparatus may authenticate the person if the presented finger is determined to be an organic body part and if the biometric sample provided by the person matches stored data associated with an authenticated identity. The stored biometric data may be a fingerprint, a spread image, a reduced template of fingerprint information, and/or a data set characterizing the spread information, etc. It can be understood that other organic body parts can be used for authentication based on similar spoof detection. For example, instead of using a fingerprint, user authentication may be based on the spoof detection described above and a matching with an image of a person's palm, face, eye ball, etc.

The present teaching discloses apparatus and methods that may distinguish a human's organic finger from a reproduction of a finger. For an organic body part, e.g. a human's finger, light can penetrate into the skin and scatter with characteristics that are difficult to recreate using non-biological materials. One of the distinguishing characteristics may be the spread of light from the directly illuminated portion of the platen into parts of the finger touching the non-directly illuminated portion of the platen. Certain spoof fingerprints (e.g. made from latex) are relatively opaque and the spread of light into the non-illuminated area will be substantially less than the spread for a genuine finger. Other spoof fingerprints (e.g. made from silicone) are relatively translucent or transparent and the spread of light into the non-illuminated area will be substantially greater than that for a genuine finger. Both situations can be detected and rejected by the apparatus disclosed in the presenting teaching.

In a practical example, an entity's database may include identities of persons (name, employee number, etc.) that are known to have authorized access to a property of the entity. Corresponding to each known identity, the database includes a pre-known fingerprint template associated with that identity. After obtaining a fingerprint from a person, the apparatus disclosed in the present teaching can determine the person's identity if the fingerprint is obtained from an organic body part and the fingerprint matches a fingerprint template associated with a known identity. Based on the determined identity of the person, the person may be allowed or denied to enter the property.

Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

FIG. 1 illustrates a conventional fingerprint reader, according to prior art. FIG. 1 shows a typical Frustrated-Total-Internal-Reflection (FTIR) optical fingerprint reader consisting of a prism 103 with a top surface 130 (forming a platen 140) upon which a finger 150 is placed, a lens with an iris 104, a CMOS (complementary metal-oxide semiconductor) image sensor 105, and a "main illumination light source(s)" 101. All imaging rays from the platen 140 toward the lens-iris 104 are at angles greater than the critical angle for a glass-air or plastic-air interface, typically 42 degreed from normal. This configuration is "dark field" because there is a black element 102 on or behind the back surface of the prism 103. Therefore, an imaging system of this reader captures a black background when nothing is present on the platen surface of the prism. The black element may be black paint on the back surface of the prism or may be a black physical piece behind the back surface of the prism. When a user touches the device with the finger 150, the user's fingerprint ridges make optical contact with the platen surface of the prism and the skin of those ridges will reflect and scatter light from the main illumination light source(s) 101, such that some of the light may be scattered toward the lens-iris 104 components. As a result, a bright image of the fingerprint ridges against a dark background is electronically captured by the CMOS image sensor 105.

Figure 2:
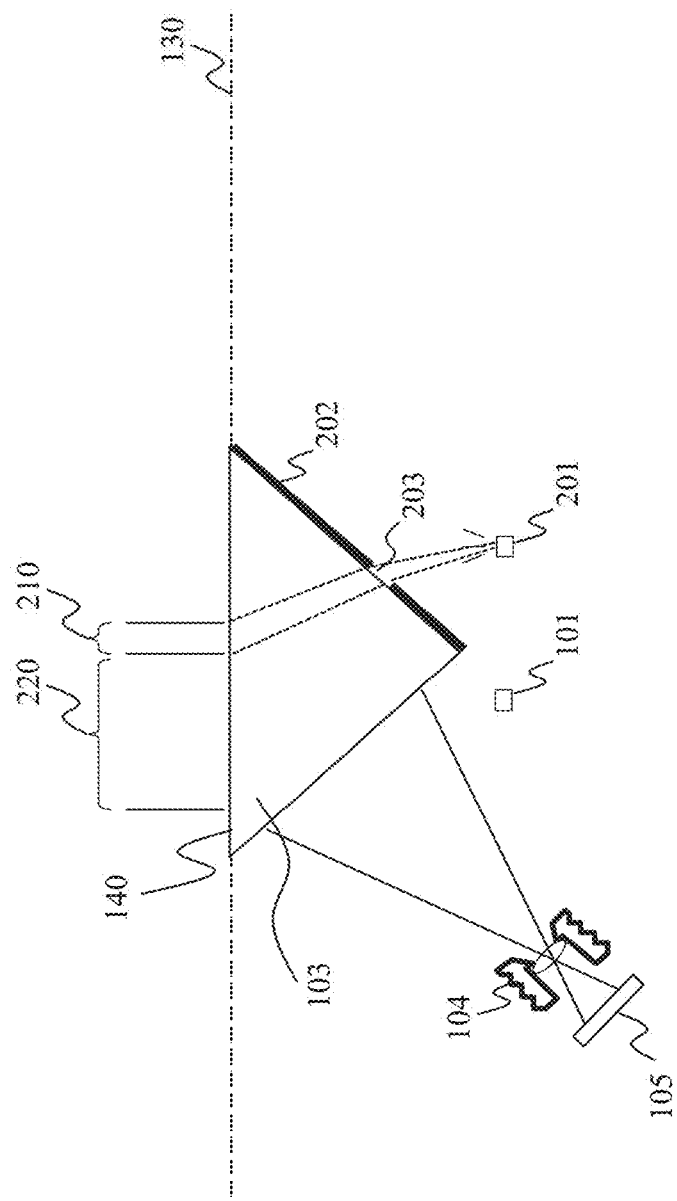
FIG. 2 illustrates a biometric reader, according to an embodiment of the present teaching.

FIG. 2 illustrates a biometric reader, according to an embodiment of the present teaching. The biometric reader in FIG. 2 is different from that in FIG. 1. As shown in FIG. 2, the black element 202 on the back surface of the prism 103 has an opening 203. An additional light source 201, hereafter referred to as the "Spoof Detection Light Source" is positioned below the opening 203 to send light through this opening and illuminate a portion of the central fingerprint area with a relatively distinct edge between the illuminated area 210 and the non-illuminated area 220. The Spoof Detection Light Source 201 may use a laser, a lens or shadow masks to create a distinct edge of the illuminated area. The light source 201 may comprise one or more LEDs (light-emitting diodes). Practical implementations of such a biometric reader may additionally have mirrors in the optical path to reduce the size of the device.

The area 210 illuminated by the Spoof Detection Light Source may be circular, rectangular or a series of spots or bars, or any other shapes alike. For example, there may be a rectangular opening in black paint on the rear surface of the prism which allows the Spoof Detection Light Source 201 to illuminate a rectangular area near the center of the platen 140. With Spoof Detection Light Source 201 on and the main illumination light source 101 off, an imaging system of the biometric reader in FIG. 2 can capture images with different characteristics depending on the object placed on the platen.

In one embodiment, the rays from the Spoof Detection Light Source 201 to the area 210 and the rays from the area 210 to imaging components, e.g. the lens-iris 104, differ by an angle of at least 45 degrees.

Figure 3:
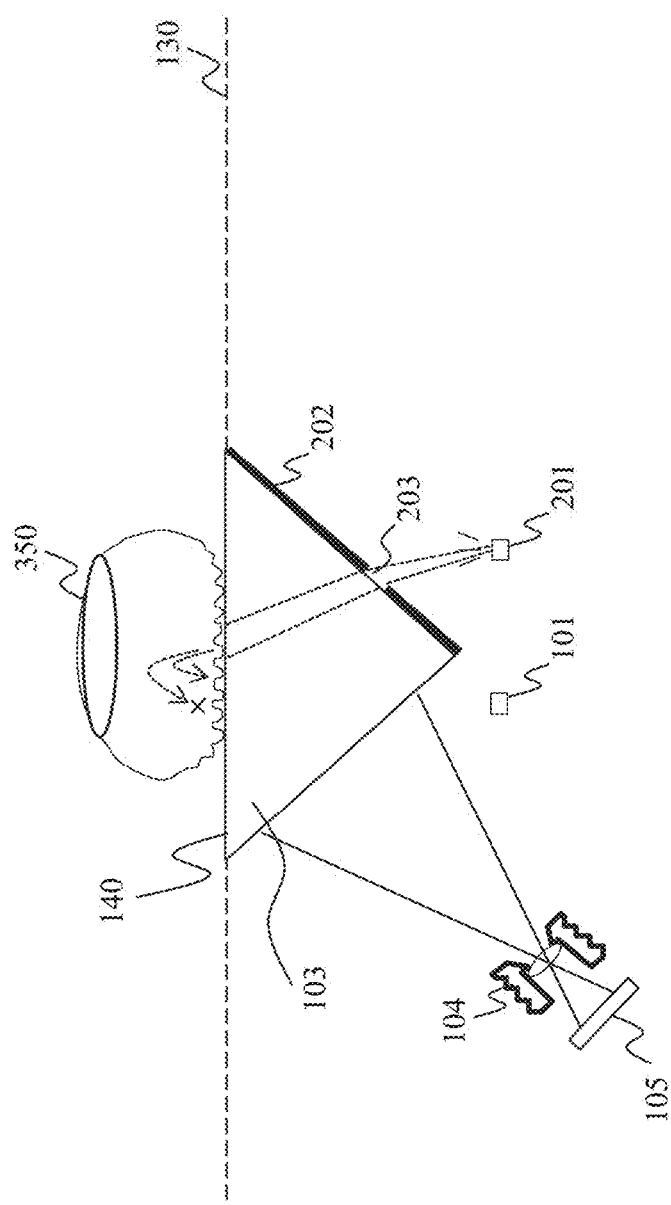
FIG. 3 illustrates a biometric reader, with a genuine finger placed on the platen, according to an embodiment of the present teaching.
Figure 4:
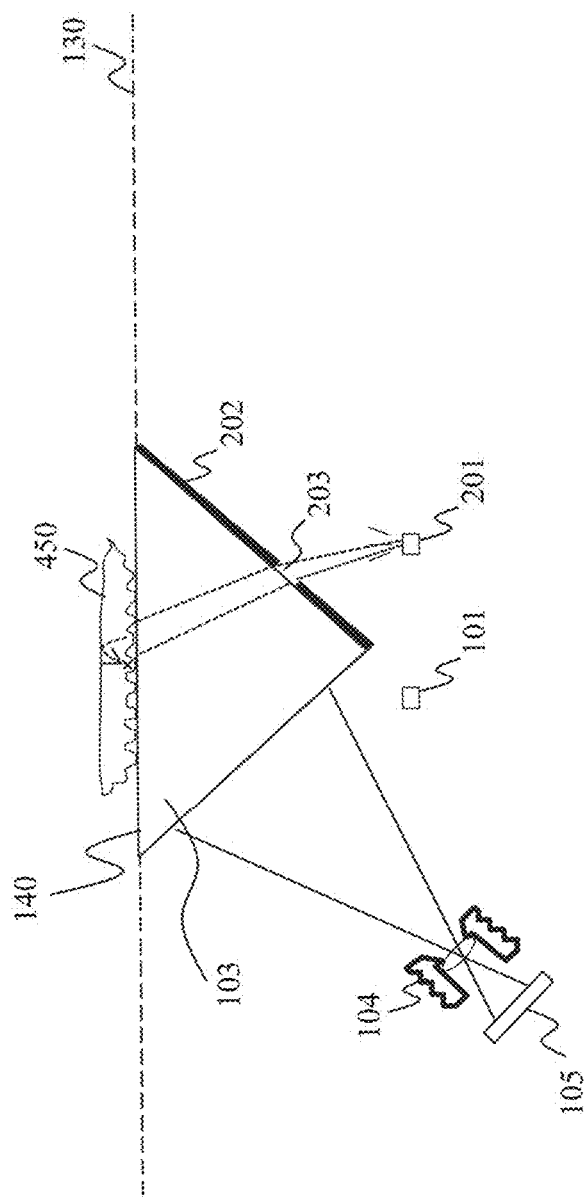
FIG. 4 illustrates a biometric reader, with an opaque object placed on the platen, according to an embodiment of the present teaching.
Figure 5:
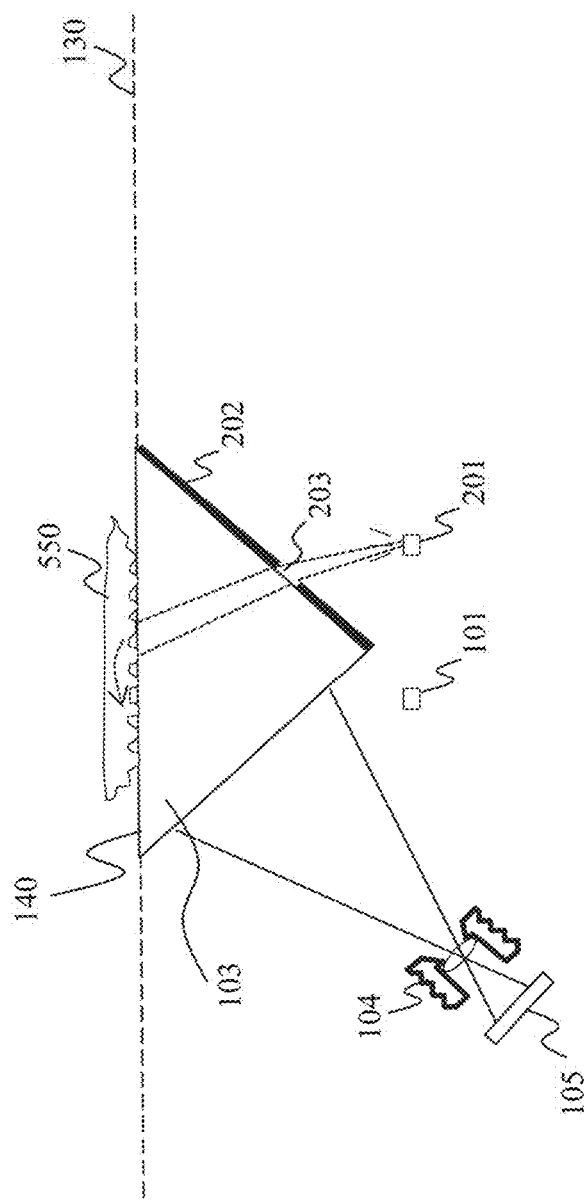
FIG. 5 illustrates a biometric reader, with a transparent or translucent object placed on the platen, according to an embodiment of the present teaching.

With nothing on the platen, the image may be relatively dark though some noise is typical in the areas illuminated by the Spoof Detection Light Source. With a true organic finger 350 placed on the platen, as shown in FIG. 3, the glow of the fingerprint ridges will extend into the non-illuminated area by a certain distance, e.g. 1 mm. With a generally opaque spoof fingerprint (such as a photocopy or a molded finger made from Latex, opaque rubber, opaque plastic, Play-Doh modeling compound, etc.), as shown in FIG. 4, the glow of fingerprint ridges will not extend very far into the non-illuminated area, e.g. by a distance of 0 to 0.5 mm. With a generally transparent or translucent spoof fingerprint (such as a molded finger made from silicone, gelatin, etc.), as shown in FIG. 5, the glow of fingerprint ridges will extend quite far into the non-illuminated area, e.g. by a distance of 2 mm or more.

With a latent fingerprint on the platen, light will generally not spread from the illuminated area into the non-illuminated area, regardless if the latent print is dusted, etc. With a latent fingerprint on the platen and an external light source such as a flashlight aimed to enhance the 'glow' of the latent print, there may be significant light signal in the non-illuminated area, but it will not have the size, shape, and roll-off characteristics of a true organic finger.

Figure 6:
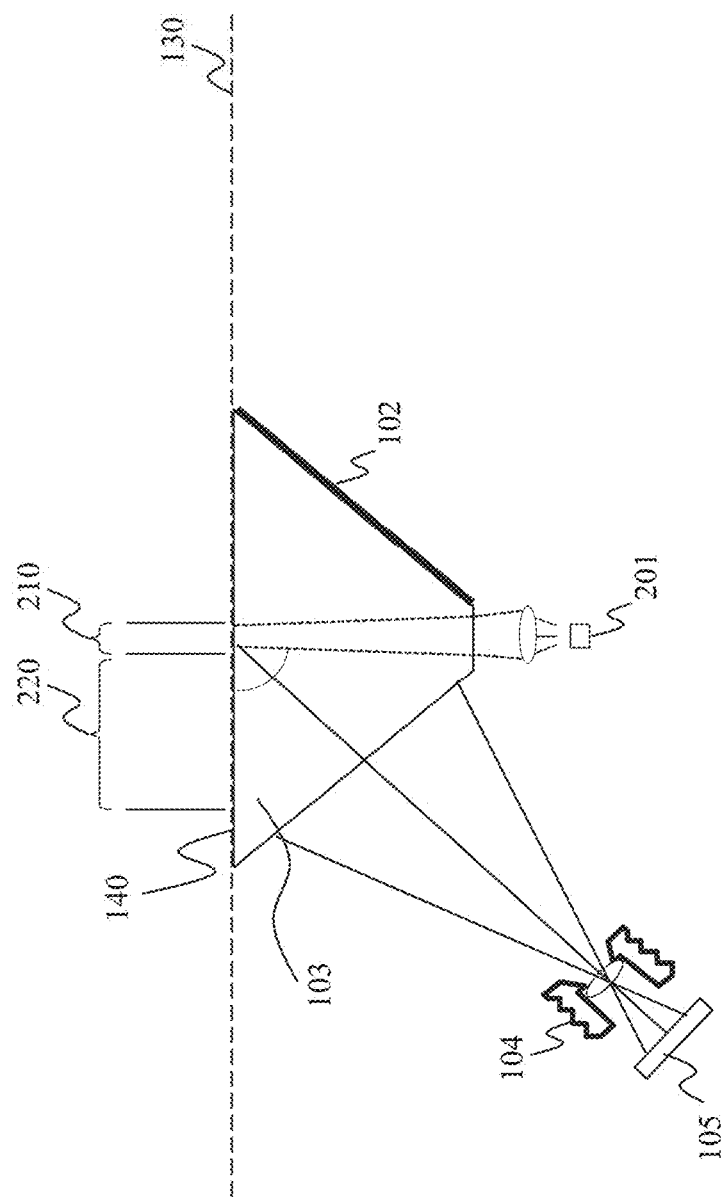
FIG. 6 illustrates a biometric reader, with a spoof detection light source located below the prism, according to an embodiment of the present teaching.
Figure 7:
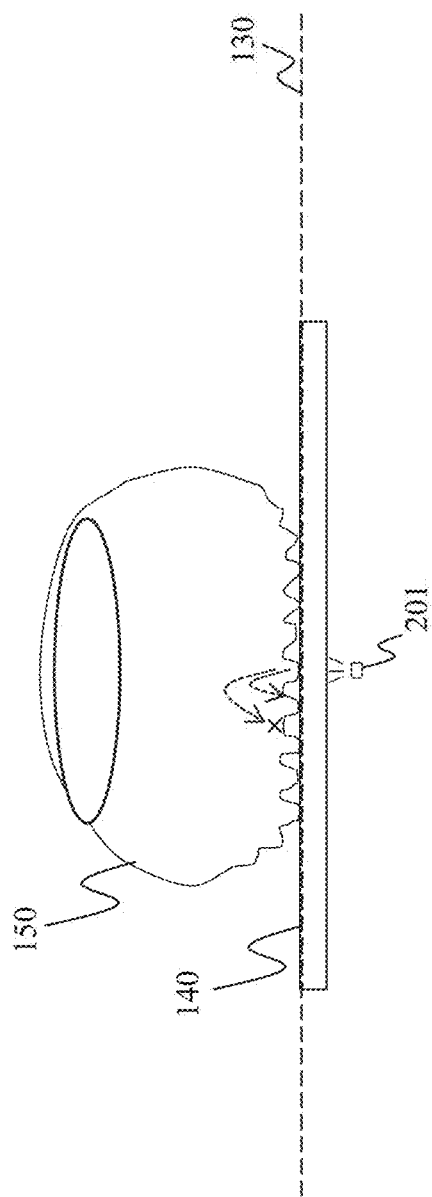
FIG. 7 illustrates a biometric reader, with a spoof detection light source located beneath the platen window, according to an embodiment of the present teaching.

It can be understood that the Spoof Detection Light Source may be placed at locations other than that shown in FIG. 2. For example, the Spoof Detection Light Source may be placed beneath the prism or platen window, or placed adjacent to the exit surface of the prism. FIG. 6 illustrates a biometric reader, with a spoof detection light source 201 located below the prism 103, according to an embodiment of the present teaching. FIG. 7 illustrates a biometric reader built upon a different imaging technology, with a spoof detection light source 201 located beneath the platen window 140, according to an embodiment of the present teaching. The size, shape, and location(s) of the illuminated areas may be hard coded into software, or programmed into the device or system during factory calibration or may be automatically determined during use.

In one embodiment of the present teaching, the biometric reader includes a single light source, such that the spread information and the fingerprint information of the object on the surface 130 can be captured simultaneously with the single light source.

While FIG. 2 shows a FTIR fingerprint reader apparatus, the present teaching works equally well in a non-FTIR fingerprint reader. Such non-FTIR fingerprint reader might use partial-internal reflection, also known as Fresnel Reflection, or may directly view the finger. Such direct viewing of the finger may be through air (non-contact method), or with the finger placed on a platen that may be flat glass or flat plastic or a prism. It can also be understood that the present teaching is applicable to hand and face readers where the imaging system directly views the subject, as opposed to through an FTIR prism.

Figure 19:
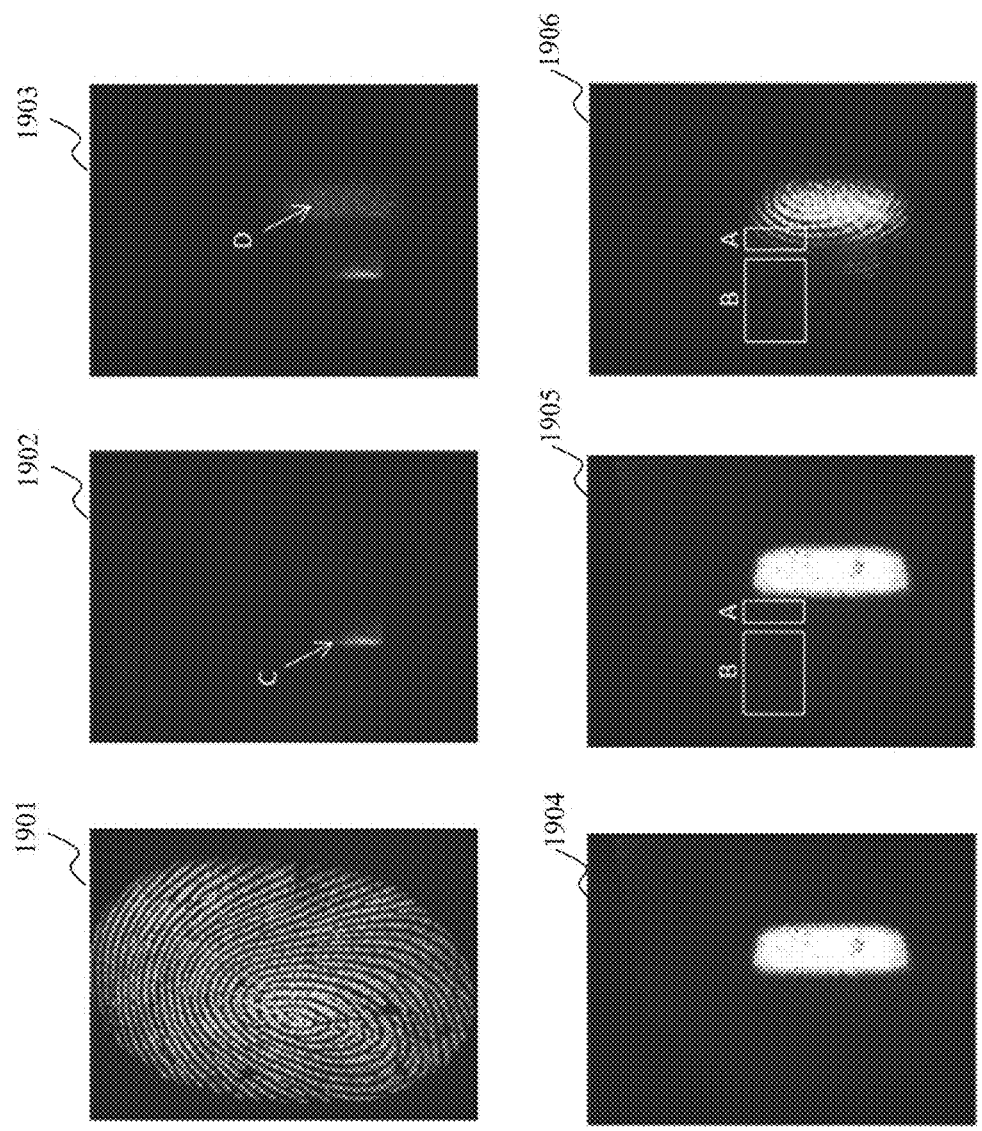
FIG. 19 illustrates sample images captured by an exemplary apparatus according to an embodiment, with a genuine finger placed on the platen.
Figure 20:
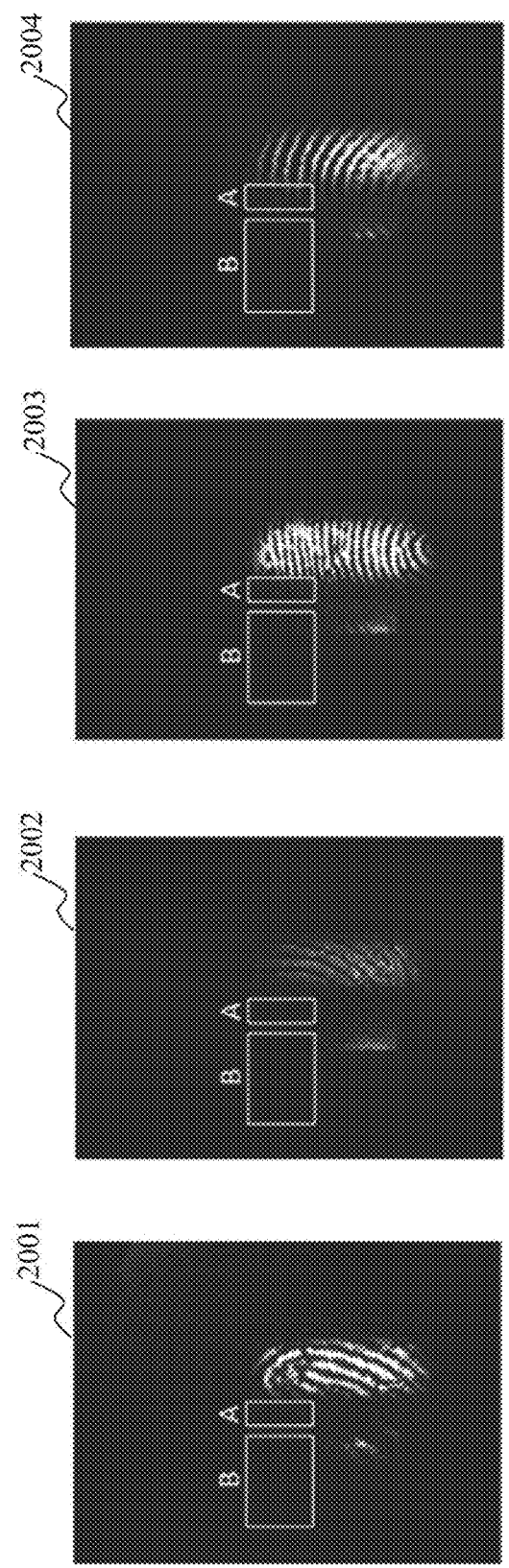
FIG. 20 illustrates sample images captured by an exemplary apparatus according to an embodiment, with opaque objects placed on the platen.
Figure 21:
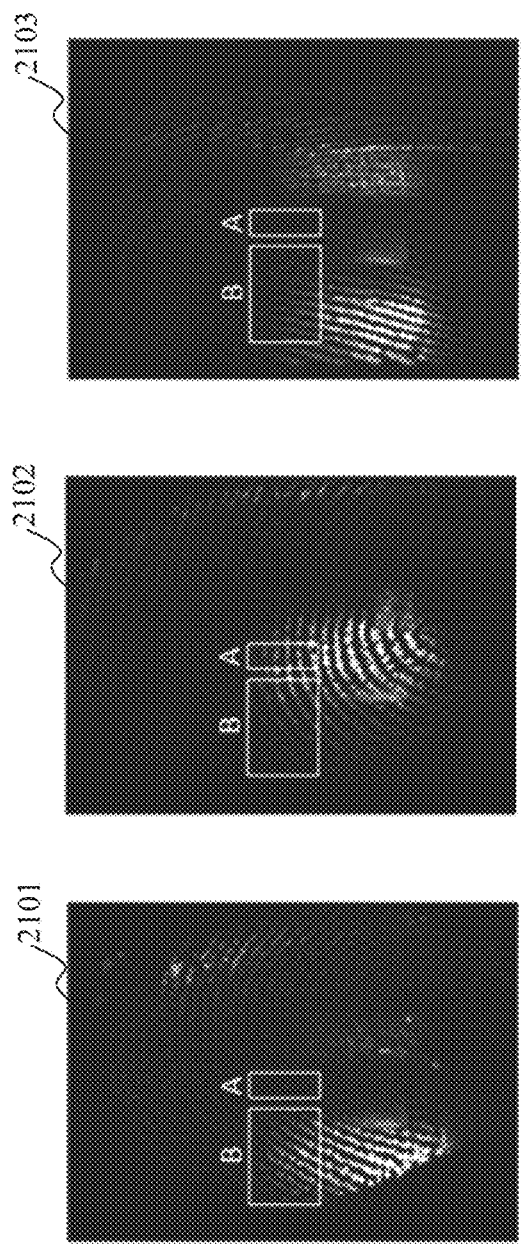
FIG. 21 illustrates sample images captured by an exemplary apparatus according to an embodiment, with transparent or translucent objects placed on the platen.

FIGS. 19-21 illustrate different sample images captured by an apparatus with construction substantially similar to that shown in FIG. 2. For scale, the total area of each of these rectangular images may be approximately 15.2×20.3 mm. In all of these images, black represents the absence of light and gray values indicate the presence and intensity of light scattered from an object on the platen toward the imaging system. Software image processing may be used to correct the characteristic geometric distortion of such a fingerprint reader to yield the geometrically correct rectangular images shown in FIGS. 19-21.

In FIG. 19, image 1901 shows a genuine finger placed on the platen and illuminated by the main illumination light source, which is a clear fingerprint image result. In other images in FIGS. 19-21, the main illumination light source is turned off and the spoof detection light source is turned on. For image 1902, the platen is clean with nothing touching it. Some small reflection signal (C) is received from the opening in the dark mask. This can be considered noise. For image 1903, the platen has some latent finger grease but no finger or spoof touching it. In addition to the small signal (C) received from the opening in the dark mask, there is some signal (D) scattered in the illuminated area of the platen. This may also be considered noise. For image 1904, white paper is placed over the entire platen with some liquid to enhance optical contact. The bright white area is the portion of the paper that receives and scatters light from the spoof detection light source, and therefore defines the 'illuminated area.' All non-white areas of this image may be considered 'non-illuminated area.' In image 1905, with the 'illuminated area' shown due to paper on the platen, two new regions of the 'non illuminated area' are defined for discussion: region A just outside the 'illuminated area' and region B farther from the 'illuminated area'. Region A is relatively narrow and Region B is somewhat wider in this example, but regions of substantially different shapes and sizes may be used in different implementations. In image 1906 and other images in FIGS. 20-21, the Regions A and B are shown in exactly the same location as defined in image 1905. In image 1906, a genuine finger is placed on the platen. Clearly a medium-strength fingerprint image signal is received in Region A while there is very little or no fingerprint image signal in Region B. This combination of results is typical of true flesh fingers and difficult to replicate with spoof materials.

FIG. 20 illustrates sample images captured by an exemplary apparatus according to an embodiment, with opaque objects placed on the platen. For image 2001, a photocopy of a fingerprint is placed on the platen (with liquid to enhance optical contact). Clearly there is very little or no fingerprint image signal in either Region A or Region B. This combination of results is typical of opaque spoof materials. For image 2002, a pink rubber stamp of a fingerprint is placed on the platen. Clearly there is very little or no fingerprint image signal in either Region A or Region B. This combination of results is typical of opaque spoof materials. For image 2003, a latex model of a fingerprint is placed on the platen. Clearly there is very little or no fingerprint image signal in either Region A or Region B. This combination of results is typical of opaque spoof materials. For image 2004, a model of a fingerprint made from Play-Doh modeling compound is placed on the platen. Clearly there is very little or no fingerprint image signal in either Region A or Region B. This combination of results is typical of opaque spoof materials.

FIG. 21 illustrates sample images captured by an exemplary apparatus according to an embodiment, with transparent or translucent objects placed on the platen. For image 2101, a model of a fingerprint made from thick clear silicone is placed on the platen. Clearly there is significant signal in Region B. This result is typical of transparent or translucent spoof materials. For image 2102, a model of a fingerprint made from thin clear silicone is placed on the platen. Clearly there is significant signal in Region B. This result is typical of transparent or translucent spoof materials. For image 2103, a model of a fingerprint made from a clear polymer rubber stamp is placed on the platen. Clearly there is significant signal in Region B. This result is typical of transparent or translucent spoof materials.

A computational system can analyze the extent of the spread of light into the non-illuminated area and make a determination that the presented image is a genuine finger or a spoof. The spread of light may be measured in several different ways all of which are envisioned by the present teaching.

The computational system may measure the distance light exceeding as threshold of intensity extends into the non-illuminated area. For example, the distance to the 50% of peak intensity point may be measured over a line or lines radiating away from the 'illuminated area.' The computational system may also measure the rate of decrease in intensity over distance. For example, the distance between the 50% of peak intensity point to 10% of peak intensity point may be measured over a line or lines radiating away from the 'illuminated area.' The computational system may define at least one region of the non-illuminated area and measure the intensity of signal over this area. The computational system may also use a combination of the above.

One skilled in the art can recognize that the measurement of spread of light could be made by comparisons to fixed values, e.g. comparison based on relative values. An example of a relative value is x percentage of a peak value measured at another specific point or area. Such relative measurements are more robust and can compensate for variations in light source intensity, color or reflectance difference in different users' skin, and other real world drifts and error sources.

The peak value for such a relative measurement may be the maximum value of a group of pixels, or may preferably be a histogram value for the group of pixels, for example the $90^{th}$ percentile of intensity for a group of pixels.

The peak value for certain measurements of light spread may preferably be measured over an area including the pixels in the 'illuminated area.' Finger oils on the platen can create a noise signal in this area which can inject errors into this measurement. One method to reduce this error is to compute pixel values by multiplying the pixel's value in the image with only the 'spoof detection light source' turned on by the same pixel's value in the image with only the 'main illumination light source' turned on. Because the pixel values in the image data under 'main illumination light source' are generally near zero in the valleys of the fingerprint and in a range of similar high values in the ridges of the fingerprint in the embodiment described here, this multiplication operation will effectively eliminate the noise signal in the valleys of the fingerprint and normalize the values for the ridges.

Although the term 'non-directly illuminated area' is used herein, it does not mean there must be zero light in the 'non-directly illuminated area'. In practical implementations of this present teaching, there may be some small amount of light in the 'non-directly illuminated area' due to leakage or other design purpose. Moreover, there could be substantial light in the 'non-directly illuminated area' that is of a different wavelength or polarization than the light from the 'spoof detection light source.' In all these cases, the spread of light through the finger from the brighter 'directly illuminated area' into the 'non-directly illuminated area' may still be measured.

In addition to simply measuring the spread of light, the system disclosed herein may additionally measure the time-varying component of the spread of light, the wavelength dependence of the spread of light, and the pressure dependence of the spread of light.

To further enhance the accuracy of the spoof determination, multiple LEDs of different wavelengths may be used or an LED which emits multiple wavelengths such as a "white LED" may be used. "White LED" may be constructed of a blue-emitting LED chip with a secondary phosphor component to re-emit light in a broad range of visible wavelengths. Red and infrared light can penetrate and scatter deeper and farther into flesh than blue and green wavelengths of light. The spread of light at these different wavelengths may be measured in the device and compared to threshold values to better distinguish genuine fingers from spoofs.

Fingertips tend to change from pink to white when pressed against a surface ("blanching"). The time-varying and pressure-varying change of the spread of light from an illuminated area into a non-illuminated area due to the blanching of the skin may also be measured and compared to values that are characteristic of genuine fingers.

The Spoof Detection Light Source may be illuminated while the Main Illumination Light Source is turned off to capture an image specifically for spoof determination, completely separate from the main fingerprint capture image.

This spread image may be taken before the reading of the main fingerprint image, or may happen after the reading of the main fingerprint image. Alternatively, the Spoof Detection Image data may be captured simultaneously with the main fingerprint image. In that situation some method may be employed to distinguish the light signal from the Spoof Detection Light Source from the light signal from the Main Illumination Light Source. That could be achieved by using different wavelengths of light for the Spoof Detection Light Source and the Main Illumination Light Source, or by analyzing the amplitude of the image signal near the boundary between the areas illuminated by, and areas non-illuminated by the Spoof Detection Light Source.

A biometric reader may incorrectly identify real fingers as spoof attempts under certain circumstances, including but not limited to: a misplaced finger (far off-center), a finger that taps too quickly (yielding little or no data under one of the illumination methods), etc. To catch such a situation, a correlation of the two images (one taken using the 'spoof detection light source' and one taken with the 'main illumination light source') may be made. The 'main illumination light source' image should be of a more uniform intensity in the borders of the 'illuminated area' than the intensity distribution in the 'spoof detection light source' image. Image data in the central area of illumination by 'spoof detection light source' should be substantially similar in fingerprint structure under both illumination methods. If not, a finger may have lifted too quickly. In portions of the 'non-illuminated area' (due to the Spoof Detection Light Source) which are used to make spoof determination measurements, (such as area A in images 1905-2103), there must be a strong fingerprint image in the image data taken with 'main illumination light source'. If not, the finger was misplaced, or moved, and an incorrect determination could result.

The present teaching may be applied in optical fingerprint readers. It is also applicable to fingerprint readers which use capacitive, thermal, RF, electric field, ultrasonic, or other technologies to read the fingerprint which are built with transparent substrates including but not limited to TFT-on-glass, TFT-on-plastic, and TFT-on-flex circuit.

The term transparent is used here to mean at least partially transparent to the wavelengths of light used for the measurements described. The wavelengths of light may be infrared and/or ultraviolet and/or visible light.

The method for reading the spread of light in the presented finger may be based on a CMOS or CCD image sensor with an imaging system including a lens. The method may alternatively be constructed using TFT-on-glass or TFT-on-plastic or TFT-on-flex technologies. Such TFT technologies might be measuring the main fingerprint image optically through the use of photodiodes or phototransistors or photo-sensors or may measure the fingerprint image using capacitive, or RF, or ultrasonic sensors built into the array. There may be at least one light source and at least one photodetector element to be built into the sensor array or positioned beneath the sensor array.

Figure 8:
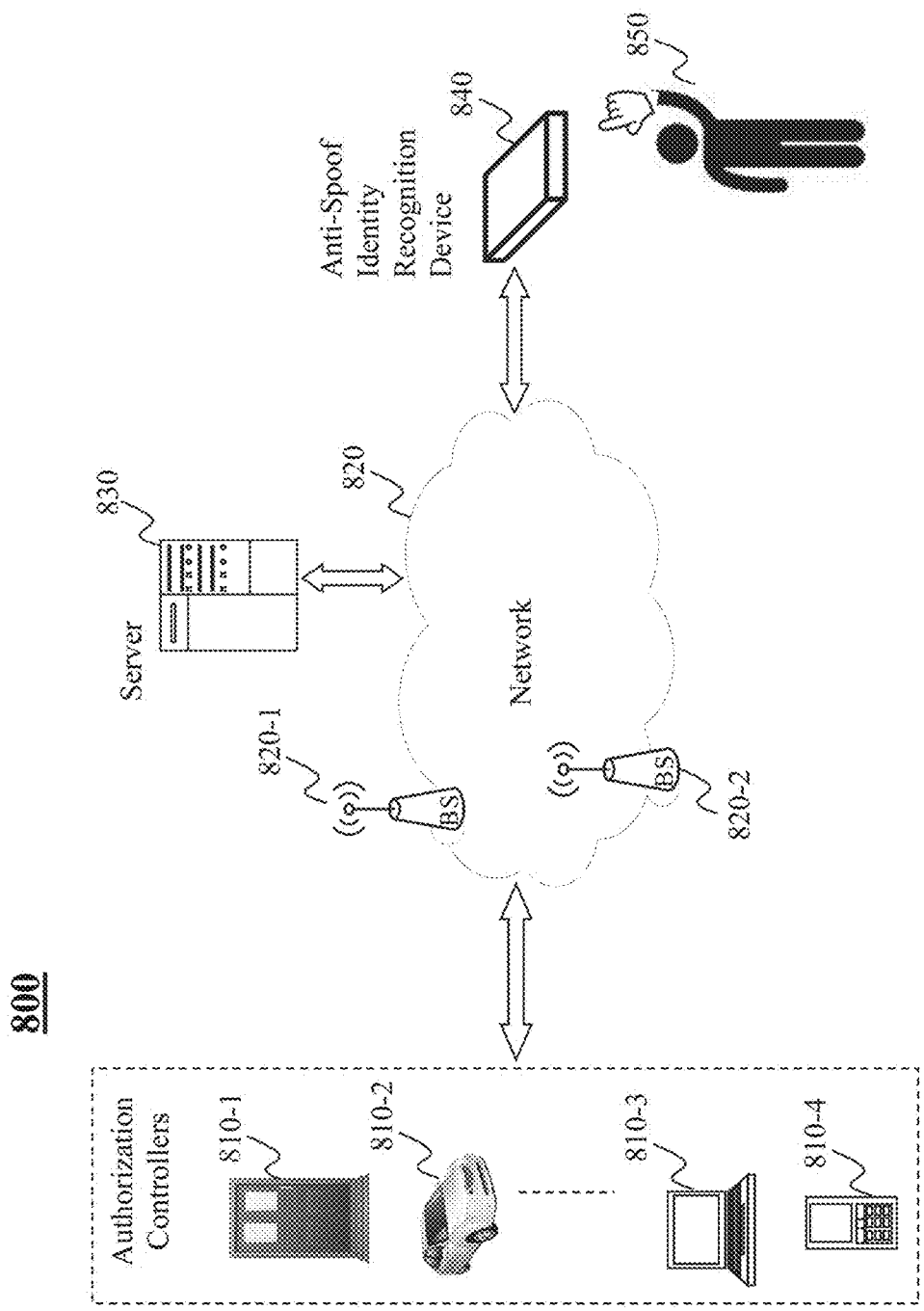
FIG. 8 is a high level depiction of an exemplary system for user identification/authentication, according to an embodiment of the present teaching.

FIG. 8 is a high level depiction of an exemplary system 800 for user identification and authorization, according to an embodiment of the present teaching. In FIG. 8, the exemplary system 800 includes a server 830, an anti-spoof identity recognition device 840, one or more authorization controllers 810, a user 850, and a network 820. The network 820 may be a single network or a combination of different networks. For example, the network 820 may be a local area network (LAN), a wide area network (WAN), a public network, a private network, a proprietary network, a Public Telephone Switched Network (PSTN), the Internet, a wireless network, a virtual network, or any combination thereof. The network 820 may also include various network access points, e.g., wired or wireless access points such as base stations or Internet exchange points 820-1 . . . 820-2, through which an authorization controller 810 may connect to the network 820 in order to obtain authorization information via the network 820.

Authorization controllers 810 may be of different types such as authorization controllers connected to a door 810-1, a car 810-2, a laptop computer 810-3, or a mobile device 810-4. A user 850 may want to access a building through a door, access a car, or access data in a laptop or a mobile device. In each case, the user 850 has to obtain access authorization from a corresponding authorization controller 810. The access authorization may be obtained by a user identification process performed at the anti-spoof identity recognition device 840 that is connected to the authorization controllers 810, e.g., directly or as shown, via the network 820.

The anti-spoof identity recognition device 840 may include the portion of a product described according to FIGS. 2-7. The anti-spoof identity recognition device 840 can acquire biometric information like a fingerprint, a spread image, or a face image of the user 850. Based on the acquired biometric information, the anti-spoof identity recognition device 840 identifies the user 850 either by itself or with the help of the server 830.

In one embodiment, the anti-spoof identity recognition device 840 identifies the user 850 by communicating with the server 830 via the network 820. This may be applicable in a case where a user wants to enter a building associated with a company that has hundreds or thousands of employees and many office buildings. In this case, user or employee data used for identifying and authorizing access may be relatively large and change very frequently. Thus, it may not be practical to have such vast data provided at each office building location. As such, user/employee data needed for identity recognition and authorization may be stored in a common server 830 and be accessible to many anti-spoof identity recognition devices 840 associated with the different office locations. For example, after an identity recognition device 840 captures and generates a fingerprint image from a finger of the user 850, the anti-spoof identity recognition device 840 may send the image to the server 830 via the network 820. The server 830 may compare the fingerprint image with images in a database implemented at the server 830. The server 830 may then send an outcome of the image comparison back to the anti-spoof identity recognition device 840 for user identification or directly to the authorization controller 810 for user authorization.

In one embodiment, the anti-spoof identity recognition device 840 captures a spread image (such as images 1905-2103 in FIGS. 19-21) from a finger of the user 850, with the Spoof Detection Light Source turned on. The anti-spoof identity recognition device 840 may determine whether the finger is genuine (organic) or not, based on the spread of light into the non-illuminated area of the spread image. The anti-spoof identity recognition device 840 may also obtain a comparison result from the server 830 that compares the fingerprint image with images in a database implemented at the server 830. Based on the spoof check determination and the fingerprint comparison result, the anti-spoof identity recognition device 840 may identify the user for the authorization controller 810 to give the user authorization or dis-recognize the user for the authorization controller 810 to deny authorization to the user. The denial may be because the finger is determined to be non-organic, or because there is no matching fingerprint in the database.

Figure 9:
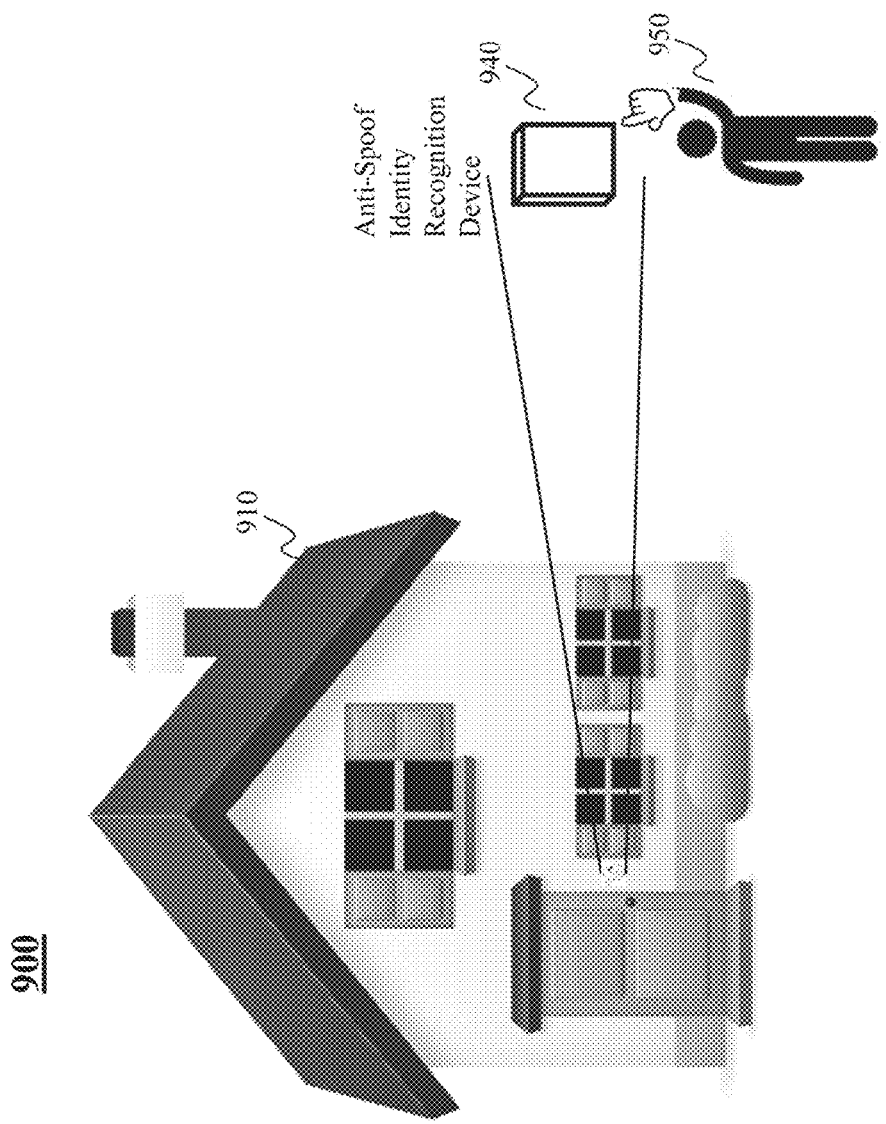
FIG. 9 is a high level depiction of another exemplary system for user identification/authentication, according to an embodiment of the present teaching.

FIG. 9 is a high level depiction of another exemplary system 900 for user identification and authorization, according to an embodiment of the present teaching. The exemplary system 900 in this embodiment includes an authorization controller 910, the anti-spoof identity recognition device 940, and a user 950. In this example, the user 950 wants to enter a building through a door which is controlled by the authorization controller 910. The anti-spoof identity recognition device 940 in this example is located near the door and can directly communicate with the authorization controller 910 without a network.

In this embodiment, the anti-spoof identity recognition device 940 may have the inherent capability to identify the user 950. This may be applicable in a case where a user wants to enter a specific building (e.g., a private residence) associated with a small group of people. In this case, user or employee data used for identifying and authorizing access may be relatively small and static, and the user identification process may not need many resources. As such, the database with user information may be implemented or provided locally at the anti-spoof identity recognition device 940. For example, after an anti-spoof identity recognition device 940 generates a fingerprint image, the anti-spoof identity recognition device 940 may compare the fingerprint image with images in the local database to obtain matching results for user identification. Based on the comparison results and spoof detection, the anti-spoof identity recognition device 940 can determine whether the user 950 has an authorization, and send the authorization information to the authorization controller 910 for authorizing access or denying access.

Figure 10:
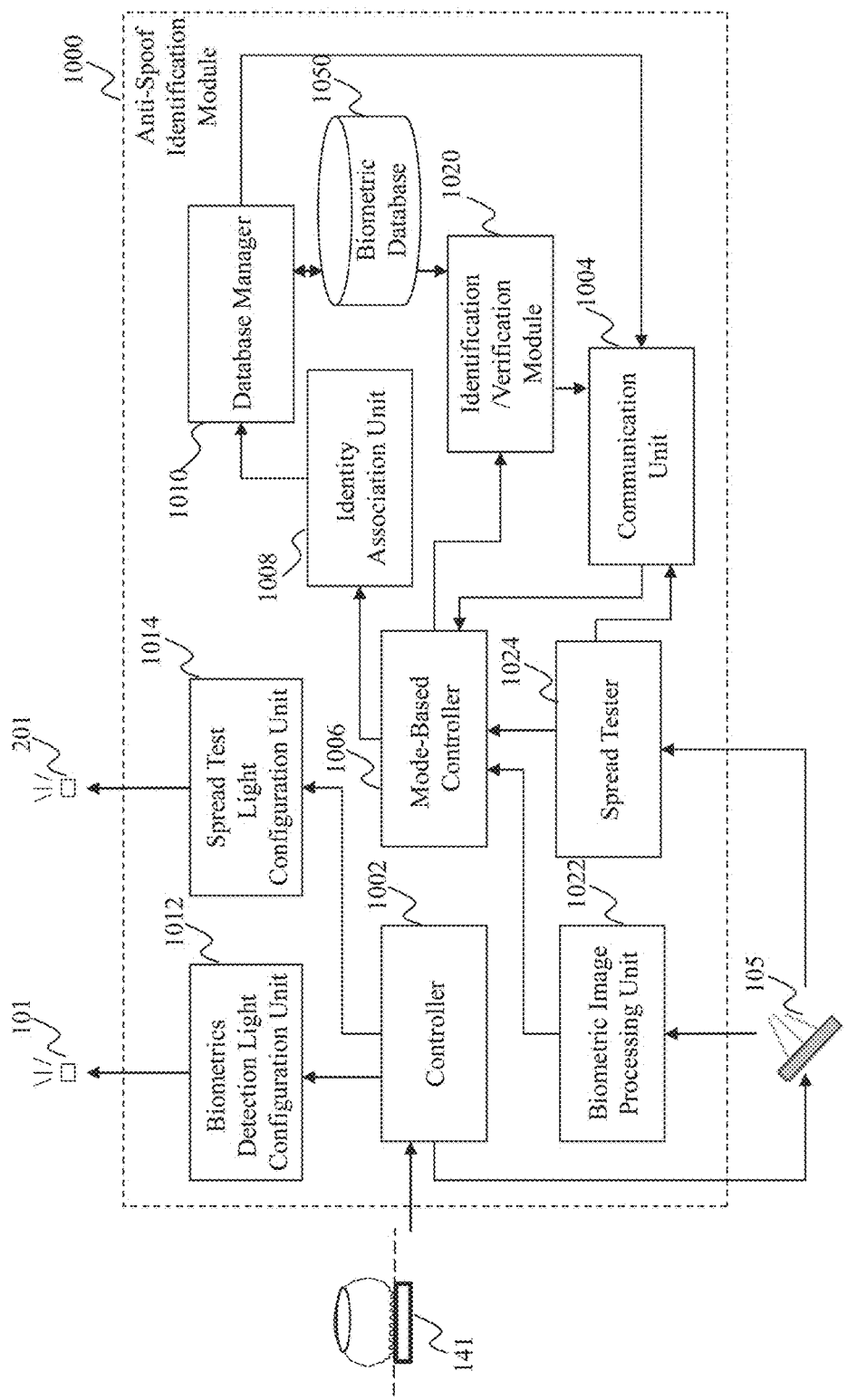
FIG. 10 illustrates an exemplary diagram of an anti-spoof identification module in a system for user identification/authentication, according to an embodiment of the present teaching.

FIG. 10 illustrates an exemplary diagram of an anti-spoof identification module 1000 in a system for user identification/authentication, according to an embodiment of the present teaching. The anti-spoof identification module 1000 may be located in the anti-spoof identity recognition device 840 shown in FIG. 8 or the anti-spoof identity recognition device 940 shown in FIG. 9. The anti-spoof identification module 1000 in this example includes a controller 1002, a biometrics detection light configuration unit 1012, a spread test light configuration unit 1014, a biometric image processing unit 1022, a spread tester 1024, a communication unit 1004, a mode-based controller 1006, an identity association unit 1008, a database manager 1010, and an identification/verification module 1020.

The controller 1002 in this example receives information from a detector 141 which may detect a finger placed on a platen of the anti-spoof identity recognition device 840 or the anti-spoof identity recognition device 940. If a finger is detected, the controller 1002 will initiate the biometrics detection light configuration unit 1012 and the spread test light configuration unit 1014 to configure the first light source 101 and the second light source 201, respectively. In one example, based on the configurations, the first light source 101 and the second light source 201 can emit lights with a same wavelength at different time slots. In another example, the first light source 101 and the second light source 201 can emit lights with different wavelengths at the same time.

In one embodiment, the controller 1002 also controls the image sensor 105 to sense the light and collect images. In another embodiment, the image sensor 105 can sense the light and collect images automatically without control from the controller 1002. In either embodiment, the image sensor 105 will generate a biometric image (e.g. an image of fingerprint, spread image, or face) and send it to the biometric image processing unit 1022 for processing, and will generate a spread image and send it to the spread tester 1024 for processing. From now on, a fingerprint image will be used as an example to describe the biometric image captured by the image sensor 105.

The biometric image processing unit 1022 in this example receives the fingerprint image from the image sensor 105 and processes the fingerprint image to generate a fingerprint template. The process of the fingerprint image includes at least extracting features including minutiae from the fingerprint image, and generating the fingerprint template based on the extracted features.

The spread tester 1024 in this example receives the spread image from the image sensor 105 and processes the spread image to determine whether the finger is an organic body part, based on a degree of light spread in the spread image. If the spread tester 1024 determines that the finger is not organic, the spread tester 1024 may generate and send a spoof notification to the communication unit 1004 such that the communication unit 1004 may inform the authorization controller or the user directly that this is not a genuine finger and access cannot be authorized. The spread tester 1024 may also send the spoof notification to the mode-based controller 1006 such that the mode-based controller 1006 may hold operations on the identity association unit 1008 and the identification/verification module 1020 because this is not an organic body part. The spread tester 1024 may also extract features from the spread image from a known organic finger, such that the processed spread image with extracted spread-related features may be an additional biometric image for recognizing the person.

The communication unit 1004 in this example may communicate with an authorization controller, which may be the authorization controller 910 or the authorization controllers 810. When a user tries to have an access controlled by the authorization controller, the authorization controller may send a user identification request to the anti-spoof identification module 1000 via the communication unit 1004. In another situation, when the system needs to collect biometric information from a user known or determined to have an access controlled by the authorization controller, the authorization controller may send a biometric recording request to the anti-spoof identification module 1000 via the communication unit 1004.

The mode-based controller 1006 in this example receives the fingerprint template from the biometric image processing unit 1022, receives the processed spread image from the spread tester 1024, and determines a work or operation mode for the anti-spoof identification module 1000 based on the request received from the authorization controller via the communication unit 1004. In one example, if the request received from the authorization controller is a "user identification" request, the mode-based controller 1006 will determine a work or operation mode to be directed to user identification. In this mode, the user's identity is unknown and needs to be determined based on the fingerprint template and the processed spread image. The mode-based controller 1006 may then forward the fingerprint template and the processed spread image to the identification/verification module 1020 for user identification or verification.

In another example, if the request received from the authorization controller is a "biometric recording" request, the mode-based controller 1006 will determine a work or operation mode to be directed to biometric recording. In this mode, the user's identity is known but the user's biometric information, e.g., the information included in the fingerprint template and/or the processed spread image needs to be recorded. The mode-based controller 1006 may then forward the fingerprint template and the processed spread image to the identity association unit 1008 for recording the biometric information.

The identity association unit 1008 in this example associates an identity with a template or an image. For example, a user's identity (e.g., name, employee number, etc.) is known and the authorization controller requests to record the user's fingerprint and spread related information. In this example, the identity association unit 1008 receives the fingerprint template and the processed spread image from the mode-based controller 1006, and associates them with the user's identity if the spread tester 1024 determines that the finger is genuine based on the processing of the spread image.

The database manager 1010 in this example receives the fingerprint template and the processed spread image associated with the user's identity from the identity association unit 1008, and saves them in a biometric database 1050 located in the anti-spoof identification module 1000. The biometric database 1050 in this example includes biometric information associated with respective user identities. The biometric information includes at least information from fingerprint templates and spread images. The fingerprint templates and spread images are stored in pairs in the biometric database 1050, where each pair corresponds to an identity. To that end, each entry in the biometric database includes identity associated with a corresponding spread image and a corresponding fingerprint template that were generated from a same finger of the user having that identity. In one embodiment, the database manager 1010 may update some biometric information in the biometric database 1050, when new biometric information from a clearer (i.e., better resolution) image associated with an existing identity is available. After the database manager 1010 saves or updates the biometric information, it may send a response to the authorization controller via the communication unit 1004 to inform the biometric information has been recorded and/or updated. It can be understood that in some embodiments, the fingerprint templates are stored in one database while the spread images are stored in another database.

The identification/verification module 1020 in this example identifies or verifies a person based on the fingerprint template and the processed spread image received from the mode-based controller 1006. In one example, when a user wants to enter a building controlled by the authorization controller, he/she directly places a finger onto a surface of the device including the anti-spoof identification module 1000 without providing other information regarding his/her identity. The identification/verification module 1020 will then identify the user based on the fingerprint template and the processed spread image. In another example, when a user wants to enter a building controlled by the authorization controller, he/she places a finger onto the device including the anti-spoof identification module 1000 after providing other information regarding his/her identity, e.g., a username input by the user or identity information in a badge scanned by the user. The identification/verification module 1020 will then verify whether the user is indeed associated with the username, based on the fingerprint template and the processed spread image.

When the identification/verification module 1020 needs to identify a user, the identification/verification module 1020 compares the fingerprint template and the processed spread image received from the mode-based controller 1006 with finger templates and spread images stored in the biometric database 1050, respectively. Since there is no other information regarding the user's identity, the order of the comparisons can be determined based on a frequency of access associated with each identity. For example, if a first identity in the biometric database 1050 has more frequent access than a second identity in the biometric database 1050, the first identity should be checked before the second identity. Accordingly, the fingerprint template and the processed spread image are compared with those associated with the first identity before being compared with those associated with the second identity. The comparison result can be determined based on a certain threshold related to a confidence score. An identity is determined when the confidence score is greater than the threshold. The confidence score can be any real number or percentage number representing a degree of matching between two templates or two images.

In one embodiment, the identification/verification module 1020 may recognize a person only based on the processed spread image received from the mode-based controller 1006. In that case, there is no need to collect fingerprint from the finger.

After identifying the user, the identification/verification module 1020 may send a response to the authorization controller via the communication unit 1004 to inform the identity of the user and whether the user should be authorized. In one embodiment, the identification/verification module 1020 merely informs the authorization controller with the identity of the user and a corresponding confidence score; while the authorization controller will determine itself whether the user should be authorized.

When the identification/verification module 1020 needs to verify a user, the identification/verification module 1020 compares the fingerprint template and the processed spread image received from the mode-based controller 1006 with a finger template and a spread image associated with the user-provide identity, e.g. the username, in the biometric database 1050 respectively. The comparison result can be determined based on a threshold related to a confidence score. The identity is verified when the confidence score is larger than the threshold. The confidence score can be any real number or percentage number representing a degree of matching between two templates or two images. After verifying the user, the identification/verification module 1020 may send a response to the authorization controller via the communication unit 1004 to inform the identity of the user is verified and whether the user should be authorized.

Figure 11:
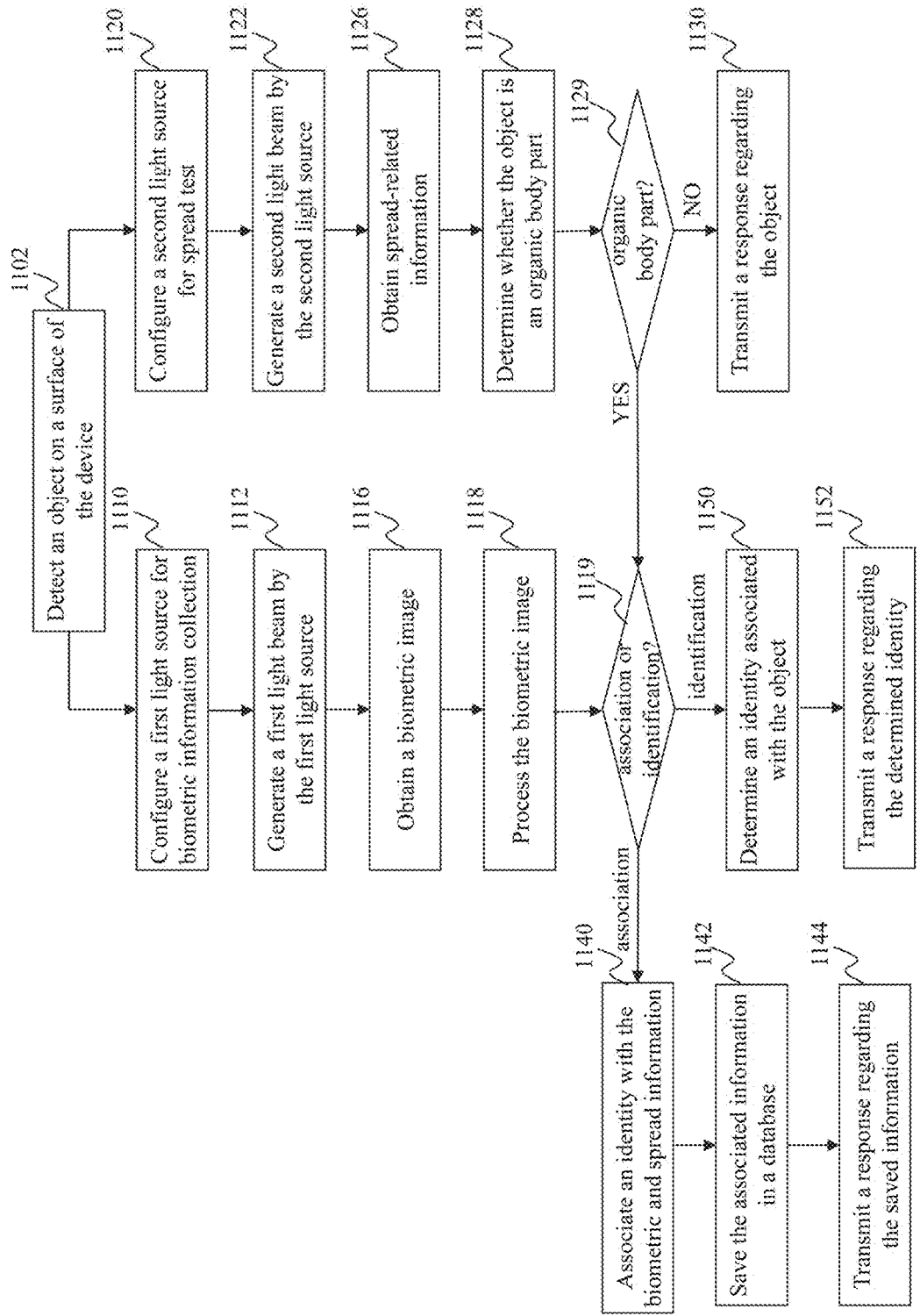
FIG. 11 is a flowchart of an exemplary process for user identification with spoof detection, according to an embodiment of the present teaching.

FIG. 11 is a flowchart of an exemplary process for user identification with spoof detection, according to an embodiment of the present teaching. In one example, the exemplary process in FIG. 11 may be performed by an exemplary device including the anti-spoof identification module 1000 shown in FIG. 10 when a user identification request is received from the authorization controller. Starting at 1102, an object is detected to be placed on a surface of the device. The process is then divided into two branches, where the two branches are performed separately.

The first branch is for biometrics collection and processing. At 1110, a first light source is configured for biometrics collection, e.g. fingerprint collection. At 1112, a first light beam is generated by the first light source according to the configuration. At 1116, a biometric image is obtained based on the sensed light. At 1118, the biometric image is processed to generate a biometric template. The process then goes to 1119.

The second branch is for spread image collection and processing. At 1120, a second light source is configured for spread image collection. At 1122, a second light beam is generated by the second light source according to the configuration. At 1126, a spread image or spread related information is obtained based on the sensed light. At 1128, the spread image is processed to determine whether the object is an organic body part. If it is determined that the object is not an organic body part at 1129, the process moves to 1130 where a response regarding the object is transmitted, e.g. a notification for spoof attack may be sent. If it is determined that the object is an organic body part at 1129, the process moves to 1119.

At 1119, the system determines that whether this is for identity association or user identification. If this is for identity association, the process goes to 1140, where an identity is associated with the biometric and spread information. Then the associated information is saved in a database at 1142. At 1144, a response regarding the saved information is transmitted.

If this is for user identification, the process goes to 1150, where an identity associated with the object is determined. The identity may be determined at 1150 based on the processed fingerprint image, the processed spread image, or both. At 1152, a response regarding the determined identity is transmitted, e.g. to an authorization controller who is interested in the identity of the person.

Figure 12:
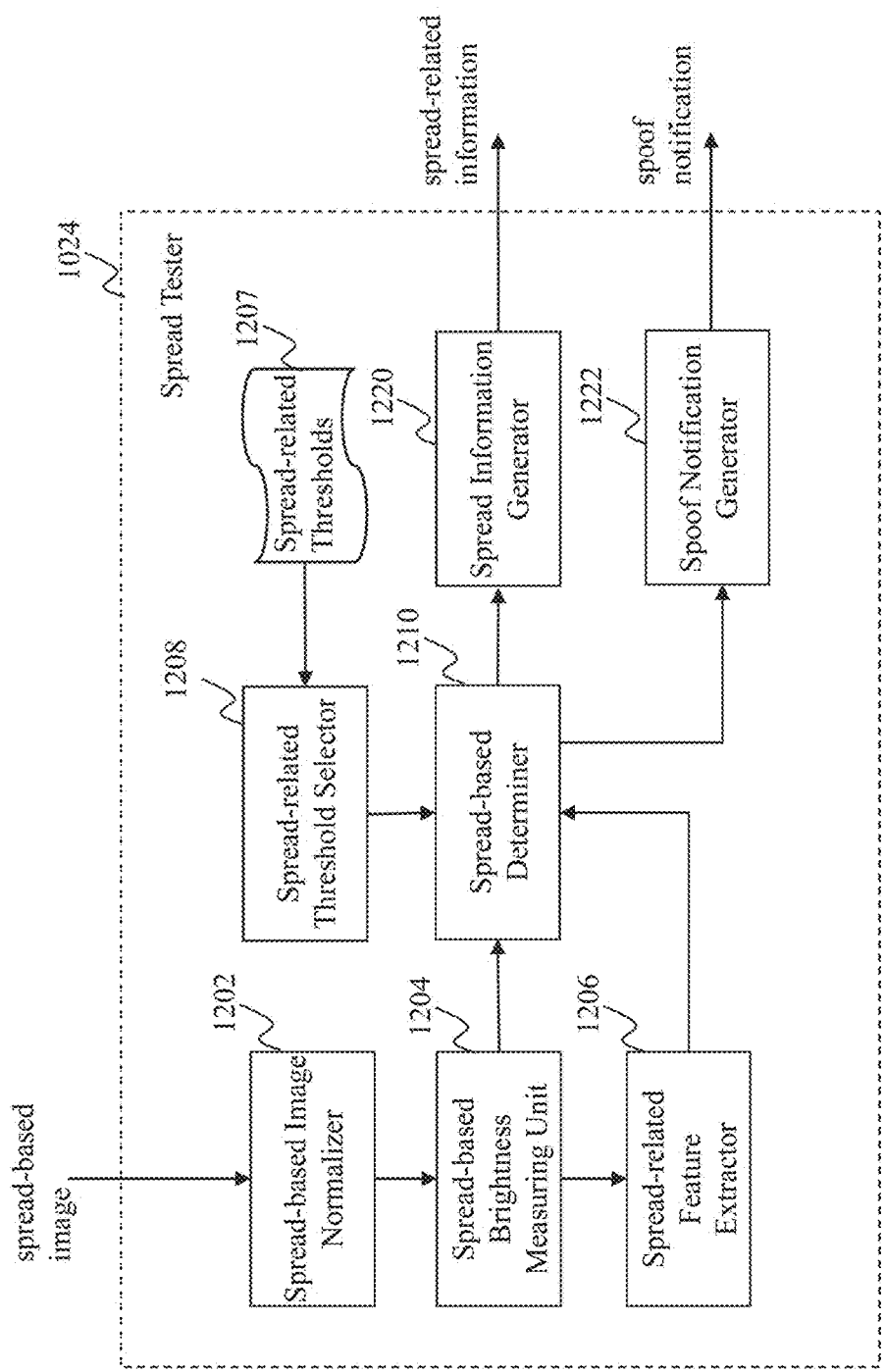
FIG. 12 illustrates an exemplary diagram of a spread tester, according to an embodiment of the present teaching.

FIG. 12 illustrates an exemplary diagram of a spread tester 1024, according to an embodiment of the present teaching. As shown in FIG. 12, the spread tester 1024 in this example includes a spread-based image normalizer 1202, a spread-based brightness measuring unit 1204, a spread-related feature extractor 1206, a spread-related threshold selector 1208, a spread-based determiner 1210, spread-related thresholds 1207, a spread information generator 1220, and a spoof notification generator 1222.

The spread-based image normalizer 1202 in this example receives a spread-based image, e.g. the images 1905-2103 in FIGS. 19-21, and normalizes geometric features (shape, size, etc.) of the spread-based image. This can help to give an accurate determination for spoof detection based on a predetermined threshold, as the geometric features may impact spread value.

The spread-based brightness measuring unit 1204 in this example can measure the spread of light into the non-illuminated area in the image. As discussed above, the measurement of spread may be based on different information in a brightness distribution in the non-illuminated area. For example, the information may include at least one of: a distance from the illuminated area to a point in the non-illuminated area where the light has a certain intensity; a distance from a first point where the light has a peak intensity to a second point in the non-illuminated area where the light has an intensity of a certain percentage of the peak intensity; a distance from a first point where the light has an intensity of a first percentage of the peak intensity to a second point where the light has an intensity of a second percentage of the peak intensity; a rate of light intensity change over distance from the illuminated area to the non-illuminated area; and a light intensity within a predetermined region in the non-illuminated area.

The spread-related feature extractor 1206 in this example may extract spread related features from the image. For example, the features may include some characteristics in a spread image, such that different spread images (e.g. image 1906 in FIG. 19) from genuine fingers can be distinguished based on their respective extracted features.

The spread-related threshold selector 1208 in this example may select one or more spread-related thresholds for spoof detection. For example, region A and region B shown in FIG. 19 are two spread-related thresholds selected for spoof detection. It can be understood that a spread-related threshold may be a line or a region with different shapes like rectangle, circle, etc.

Based on the spread-related thresholds and the brightness distribution of the spread image, the spread-based determiner 1210 may determine whether the object is an organic body part. As discussed above, a spread image of non-organic material may have different spread information than that of a spread image of an organic body part.

If the spread-based determiner 1210 determines that the object is an organic body part, the spread information generator 1220 may generate and send spread-related information for either identity association or user identification. If the spread-based determiner 1210 determines that the object is not an organic body part, the spoof notification generator 1222 may generate and send a spoof notification for noticing that there is a spoof attack or the object put on the platen is not an organic body part.

Figure 13:
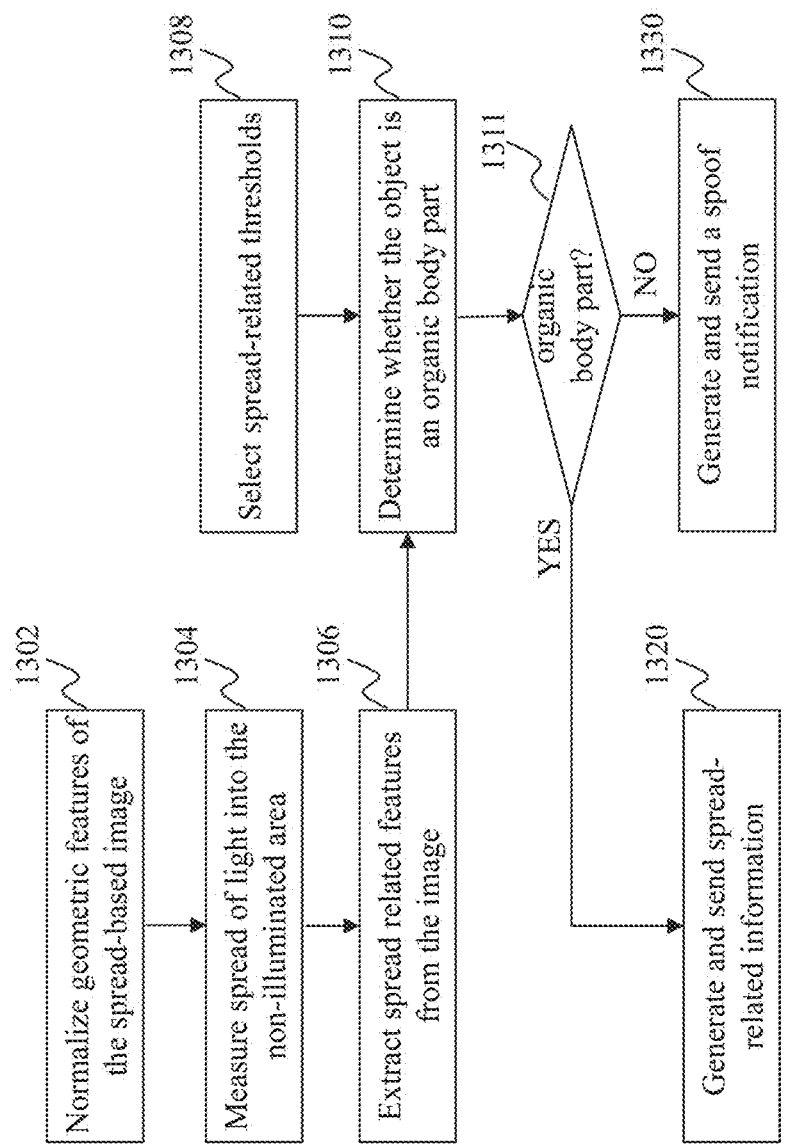
FIG. 13 is a flowchart of an exemplary process performed by a spread tester, according to an embodiment of the present teaching.

FIG. 13 is a flowchart of an exemplary process performed by a spread tester, according to an embodiment of the present teaching. Geometric features of a spread-based image are normalized at 1302. Spread of light into the non-illuminated area is measured at 1304. Spread related features are extracted from the image at 1306. The process then moves to 1310.

At 1308, one or more spread-related thresholds are selected. The process then moves to 1310. At 1310, it is determined whether the object is an organic body part, based on the measured spread and the spread-related thresholds. If it is determined that the object is an organic body part at 1311, spread-related information is generated and sent at 1320. If it is determined that the object is not an organic body part at 1311, a spoof notification is generated and sent at 1330.

Figure 14:
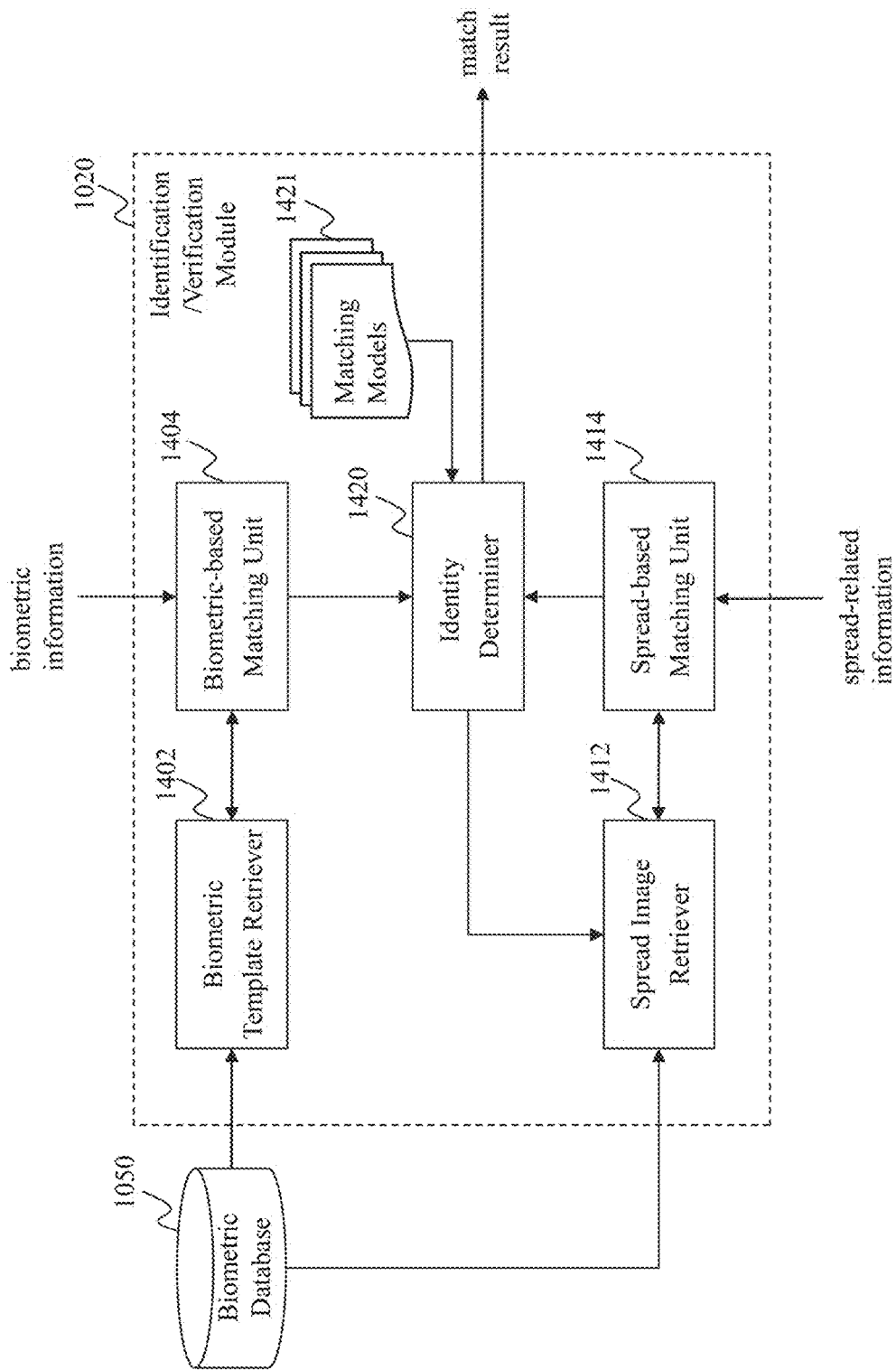
FIG. 14 illustrates an exemplary diagram of an identification/verification module, according to an embodiment of the present teaching.

FIG. 14 illustrates an exemplary diagram of an identification/verification module 1020 in a system for user identification, according to an embodiment of the present teaching. In one embodiment, the identification/verification module 1020 may be located in the anti-spoof identification module 1000 in FIG. 10. The identification/verification module 1020 in this example includes a biometric template retriever 1402, a biometric-based matching unit 1404, a spread image retriever 1412, a spread-based matching unit 1414, matching models 1421, and an identity determiner 1420.

The biometric-based matching unit 1404 in this example receives a biometric template, e.g. a fingerprint template, and some related information from the mode-based controller 1006. The related information may include whether this is for user identification without known identity or for user verification with a user-provided identity. The biometric-based matching unit 1404 may then inform the biometric template retriever 1402 to retrieve one or more fingerprint templates from the biometric database 1050.

The biometric template retriever 1402 in this example retrieves the one or more fingerprint templates from the biometric database 1050, according to instructions received from the biometric-based matching unit 1404. In one example, the identification/verification module 1020 works for user identification. In another example, the identification/verification module 1020 works for user verification with a user-provided identity.

The biometric-based matching unit 1404 compares the fingerprint template received from the mode-based controller 1006 with each retrieved fingerprint template to generate a comparison result with a confidence score. The confidence score indicates how likely the fingerprint template matches the retrieved fingerprint template associated with an identity. In one example, the confidence score is generated based on the matching score that represents a similarity between the two templates. The confidence score can be any real number or percentage number representing a degree of matching between two fingerprint templates. An identity may be determined when a fingerprint template associated with the identity matches the received fingerprint template with a confidence score larger than a pre-determined threshold. The biometric-based matching unit 1404 sends the comparison results to the identity determiner 1420 for identity determination.

The identity determiner 1420 in this example determines an identity based on the comparison results in accordance with one of the matching models 1421 stored in the identification/verification module 1020. Each matching model 1421 may determine a manner in which an identity is determined. According to one matching model, the identity determiner 1420 may determine an identity based on the fingerprint template when the finger is determined to be genuine. According to another matching model, the identity determiner 1420 may determine an identity based on the fingerprint template and spread features from a spread image of the same finger after the finger is determined to be genuine. In that case, the identity determiner 1420 may inform the spread image retriever 1412 to retrieve spread images for spread image matching at 1414.

The spread image based matching unit 1414 in this example receives a processed spread image and some related information from the mode-based controller 1006. The related information may include whether this is for user identification without known identity or for user verification with a user-provided identity. The spread image based matching unit 1414 may then inform the spread image retriever 1412 to retrieve one or more spread images from the biometric database 1050.

The spread image retriever 1412 in this example retrieves one or more spread images from the biometric database 1050, according to instructions received from the spread image based matching unit 1414. The spread image based matching unit 1414 compares the processed spread image received from the mode-based controller 1006 with each retrieved spread image to generate a comparison result with a confidence score. The confidence score indicates how likely the processed spread image matches the retrieved spread image associated with an identity. The confidence score can be any real number or percentage number representing a degree of matching between two spread images. The spread image based matching unit 1414 sends the comparison results to the identity determiner 1420 for identity determination.

In one embodiment, the biometric template retriever 1402 and the spread image retriever 1412 can communicate and align with each other so that a pair of fingerprint template and spread image associated with an identity is retrieved together by the biometric template retriever 1402 and the spread image retriever 1412 respectively.

The identity determiner 1420 in this example determines an identity based on the comparison results from the biometric-based matching unit 1404 and the spread image based matching unit 1414, in accordance with one of the matching models 1421 stored in the identification/verification module 1020.

In accordance with a first embodiment, an identity of a person is determined to be a known identity if the processed spread image matches a spread image associated with the known identity in the database and the fingerprint template matches a fingerprint template associated with the same known identity in the database.

In accordance with a second embodiment, an identity of a person is determined to be a known identity if either the processed spread image matches a spread image associated with the known identity in the database or the fingerprint template matches a fingerprint template associated with the same known identity in the database.

In accordance with a third embodiment, a person is first identified as an identity having highest confidence score for fingerprint. If there are multiple identities having the same highest confidence score for fingerprint, the person is then identified as the identity having highest confidence score for spread image among the multiple identities.

In accordance with a fourth embodiment, a person is first identified as an identity having highest confidence score for spread image. If there are multiple identities having the same highest confidence score for spread image, the person is then identified as the identity having highest confidence score for fingerprint among the multiple identities.

For any matching model in any embodiment, if there are multiple identities having the same two confidence scores, the identity determiner 1420 may report the multiple identities together. In this situation, the system may instruct the user to place the finger again or place another finger for identification.

The identity determiner 1420 then sends a matched result to the authorization controller. The matched result may include the determined identity and an associated confidence score. In one embodiment, the matched result may include a decision about whether the person should be authorized or not.

Figure 15:
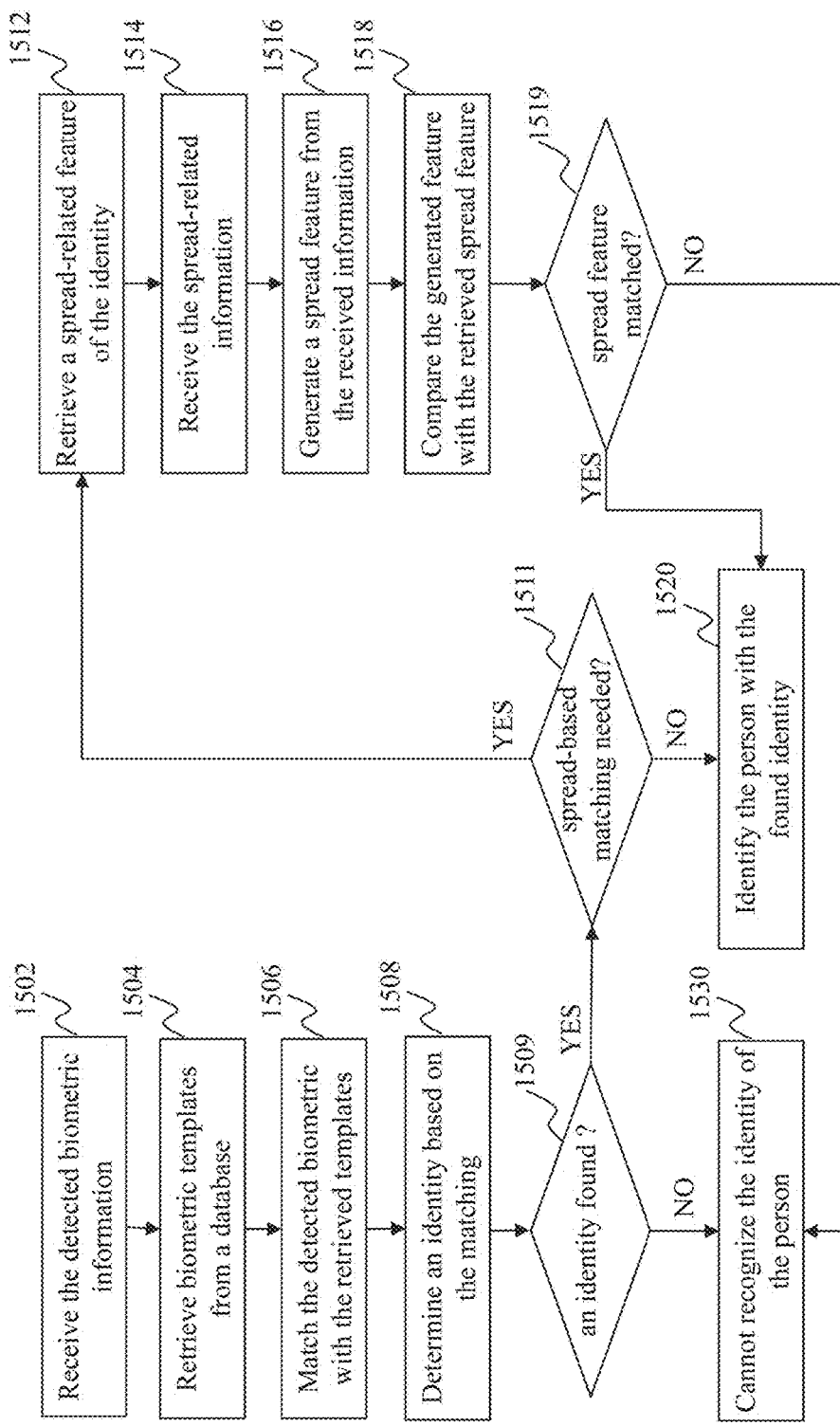
FIG. 15 is a flowchart of an exemplary process performed by an identification/verification module, according to an embodiment of the present teaching.

FIG. 15 is a flowchart of an exemplary process performed by an identification/verification module, e.g. the identification/verification module 1020 in the FIG. 14, according to an embodiment of the present teaching. At 1502, detected biometric information, e.g. a fingerprint template, is received. At 1504, biometric templates are retrieved from a database. At 1506, the detected biometric is matched with the retrieved biometric templates. At 1508, the identification/verification module 1020 try to determine one or more identities each with a confidence score based on the biometric matching. At 1509, if there is no identity found based on the biometric matching, the process goes to 1530 to determine the identity of the person cannot be recognized. At 1509, if there is an identity found based on the biometric matching, the process goes to 1511, where it is determined whether a spread-based matching is needed.

If at 1511, it is determined that there is no need for spread-based matching, the process goes to 1520, where the person is identified with the found identity based on biometric matching. If at 1511, it is determined that there is a need for spread-based matching, the process goes to 1512. This may happen when the system wants a higher security level.

At 1512, a spread-related feature, e.g. a degree of spread, of the found identity is retrieved from a database. The spread-related information is received at 1514 from the same object, e.g. a spread image of the same finger is obtained with the Spoof Detection Light Source turned on and the main illumination light source turned off. At 1516, a spread feature, e.g. a degree of spread, is generated from the received spread image. At 1518, the generated feature is compared with the retrieved spread feature. At 1519, it is determined whether there is a spread feature match. If so, the process goes to 1520, where the person is identified with the found identity based on biometric matching and the spread-based matching. If it is determined there is not a spread feature match at 1519, the process goes to 1530 to determine the identity of the person cannot be recognized.

Figure 16:
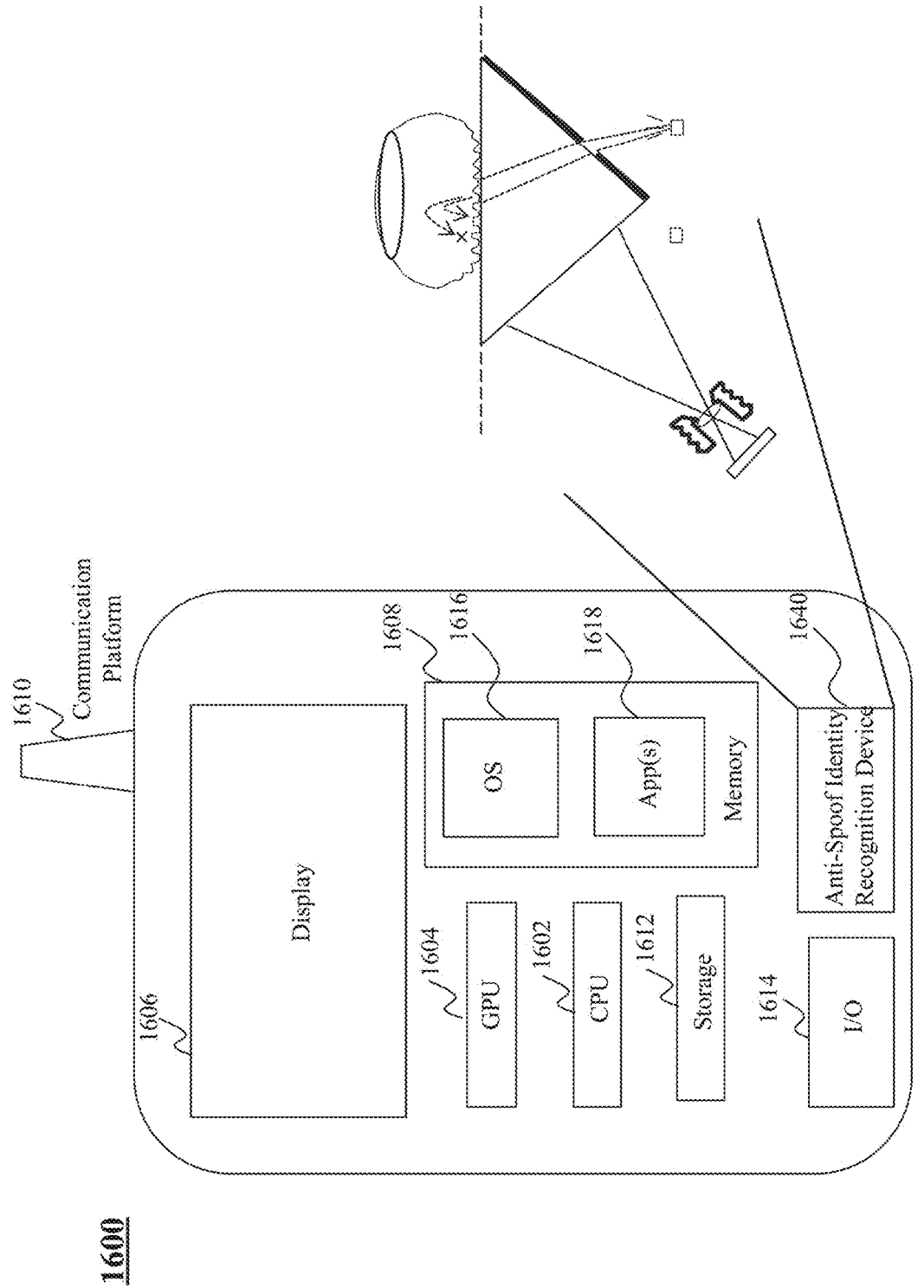
FIG. 16 depicts a general mobile device architecture on which the present teaching can be implemented.

FIG. 16 depicts a general mobile device architecture on which the present teaching can be implemented. In one example, the authorization controller 810-4 controls access to a mobile device 1600, including but is not limited to, a smart phone, a tablet, a music player, a handled gaming console, a GPS receiver. The mobile device 1600 in this example includes one or more central processing units (CPUs) 1602, one or more graphic processing units (GPUs) 1604, a display 1606, a memory 1608, a communication platform 1610, such as a wireless communication module, storage 1612, and one or more input/output (I/O) devices 1614. Any other suitable component, such as but not limited to a system bus or a controller (not shown), may also be included in the mobile device 1600. As shown in FIG. 16, a mobile operating system 1616, e.g., iOS, Android, Windows Phone, etc., and one or more applications 1618 may be loaded into the memory 1608 from the storage 1612 in order to be executed by the CPU 1602. The applications 1618 may include a web browser or any other suitable mobile search apps. Execution of the applications 1618 may cause the mobile device 1400 to perform some processing as described before.

In another example, an anti-spoof identity recognition device 1640 according to various embodiments in the present teaching can be integrated in the mobile device 1600. The anti-spoof identity recognition device 1640 may include the anti-spoof identification module 1000 shown in FIG. 10 for spoof detection. In this example, a user's identity may be determined or verified by placing a finger on the identity recognition device 1640 on the mobile device 1600. The user identification in this example may be used for a user to obtain access to either the mobile device 1600 or another device, e.g. a car or a controller at a door that can communicate with the mobile device 1600.

To implement the present teaching, computer hardware platforms may be used as the hardware platform(s) for one or more of the elements described herein. The hardware elements, operating systems, and programming languages of such computers are conventional in nature, and it is presumed that those skilled in the art are adequately familiar therewith to adapt those technologies to implement the processing essentially as described herein. A computer with user interface elements may be used to implement a personal computer (PC) or other type of work station or terminal device, although a computer may also act as a server if appropriately programmed. It is believed that those skilled in the art are familiar with the structure, programming, and general operation of such computer equipment and as a result the drawings should be self-explanatory.

Figure 17:
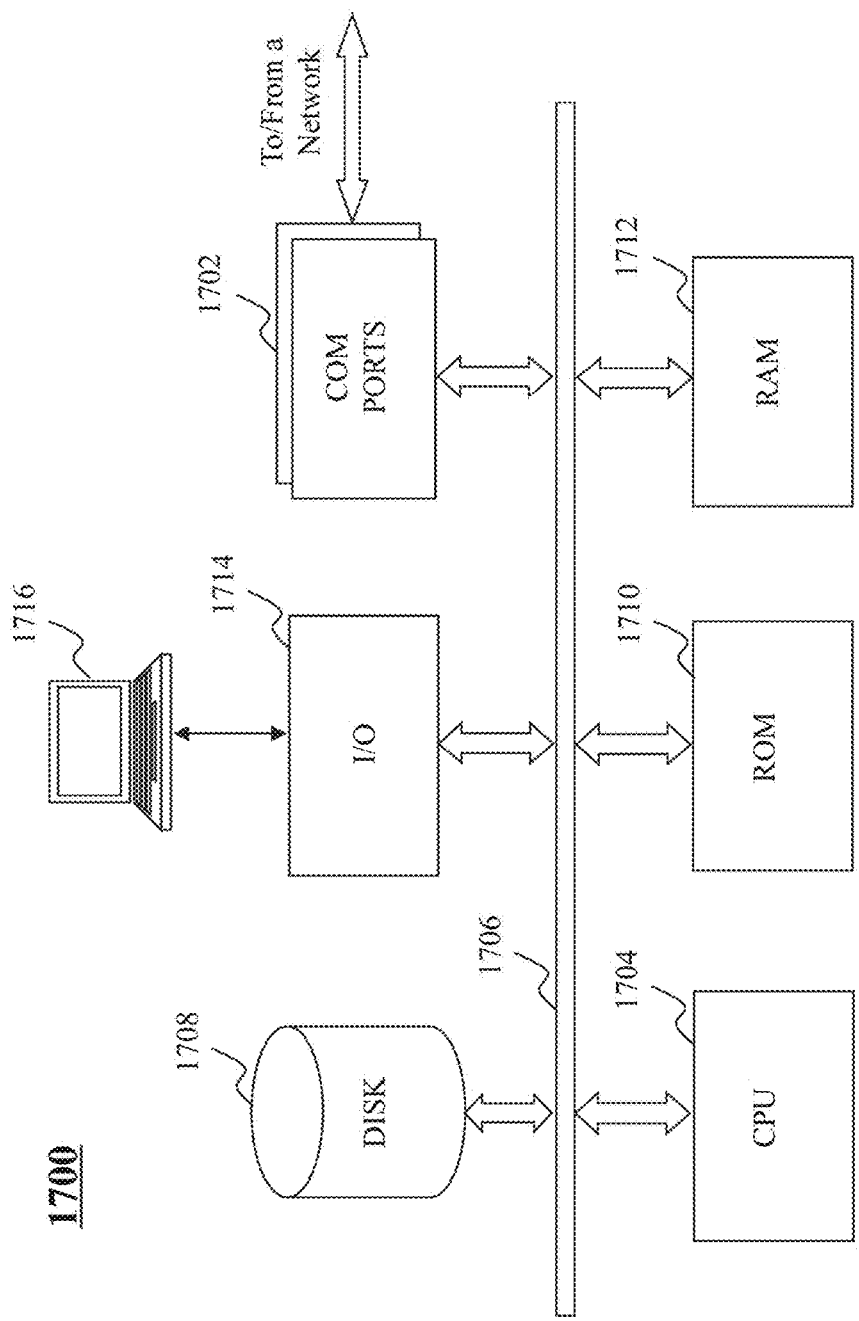
FIG. 17 depicts a general computer architecture on which the present teaching can be implemented.

FIG. 17 depicts a general computer architecture on which the present teaching can be implemented and has a functional block diagram illustration of a computer hardware platform that includes user interface elements. The computer may be a general purpose computer or a special purpose computer. This computer 1700 can be used to implement any components of the user identification architecture as described herein. Different components of the system, e.g., as depicted in FIGS. 2-15, can all be implemented on one or more computers such as computer 1700, via its hardware, software program, firmware, or a combination thereof. Although only one such computer is shown, for convenience, the computer functions relating to user identification may be implemented in a distributed fashion on a number of similar platforms, to distribute the processing load.

The computer 1700, for example, includes COM ports 1702 connected to and from a network connected thereto to facilitate data communications. The computer 1700 also includes a CPU 1704, in the form of one or more processors, for executing program instructions. The exemplary computer platform includes an internal communication bus 1706, program storage and data storage of different forms, e.g., disk 1708, read only memory (ROM) 1710, or random access memory (RAM) 1712, for various data files to be processed and/or communicated by the computer, as well as possibly program instructions to be executed by the CPU 1704. The computer 1700 also includes an I/O component 1714, supporting input/output flows between the computer and other components therein such as user interface elements 1716. The computer 1700 may also receive programming and data via network communications.

Hence, aspects of the method of user identification, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media can take the form of electric or electromagnetic signals, or acoustic or light waves such as those generated during radio frequency (RF) and infrared (IR) data communications. Common forms of computer-readable media therefore may include for example: a hard disk, a CD-ROM, DVD or DVD-ROM, any other optical medium, a FLASH memory, any other memory chip, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Figure 18:
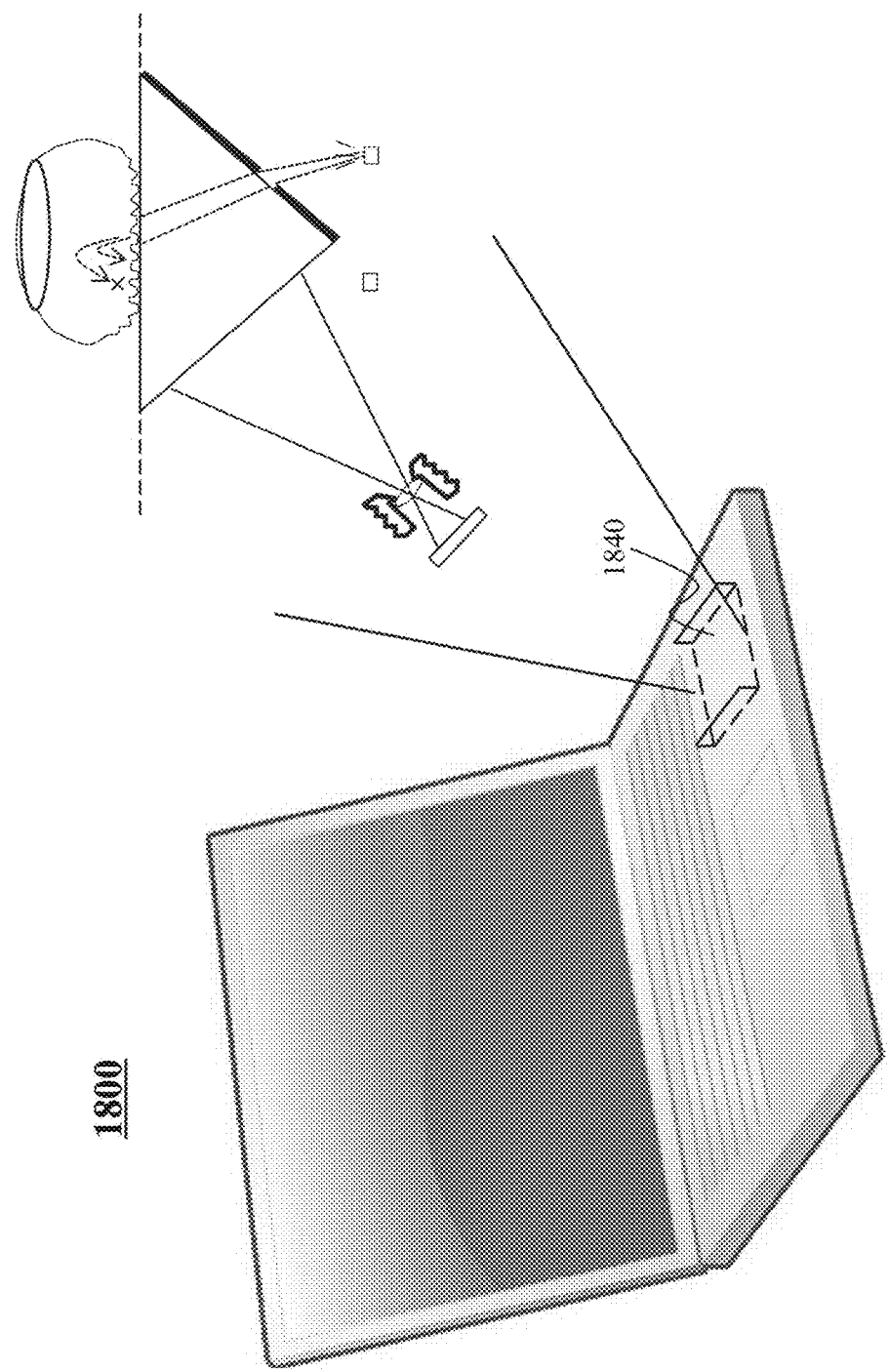
FIG. 18 depicts an exemplary manner in which the present teaching can be implemented on a general computer.

FIG. 18 depicts an exemplary manner in which the present teaching can be implemented on a general computer. In this example, an anti-spoof identity recognition device 1840 according to various embodiments in the present teaching can be integrated in a laptop 1800. In this example, a user's identity may be determined or verified by placing a finger on the anti-spoof identity recognition device 1840 on the laptop 1800, with spoof detection. The user identification in this example may be used for a user to obtain access to either the laptop 1800 or another device, e.g. a car or a controller at a door that can communicate with the laptop 1800.

Those skilled in the art will recognize that the present teachings are amenable to a variety of modifications and/or enhancements. For example, although the implementation of various components described above may be embodied in a hardware device, it can also be implemented as a software only solution—e.g., an installation on an existing server. In addition, the units of the host and the client nodes as disclosed herein can be implemented as a firmware, firmware/software combination, firmware/hardware combination, or a hardware/firmware/software combination.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

I claim:

1. An apparatus, comprising:
 a surface on which an object is placed;
 a first light source configured for providing a first light illuminating a portion of the surface, wherein the object spreads the first light shone on the portion to a disjoint area of the surface;
 a brightness measuring unit configured for measuring a degree to which the light is spread into the disjoint area; and
 a determiner configured for determining whether the object is an organic body part based on the measured degree.

2. The apparatus of claim 1, further comprising a threshold selector configured for selecting one or more thresholds based on a predetermined brightness distribution caused by an organic body part spreading light shone thereon to a disjoint area, wherein the determiner determines whether the object is an organic body part by comparing the measured degree with the one or more thresholds.

3. The apparatus of claim 1, wherein the measured degree comprises information of at least one of the following:
 a distance from the portion to a point in the disjoint area where the spread light has a certain intensity;
 a distance from a first point in the portion where the light has a peak intensity to a second point in the disjoint area where the spread light has an intensity of a certain percentage of the peak intensity;
 a distance from a first point where the light in the portion has an intensity of a first percentage of the peak intensity to a second point in the disjoint area where the spread light has an intensity of a second percentage of the peak intensity;
 a rate of light intensity change over distance from the portion to the disjoint area; and
 a light intensity computed within a predetermined region in the disjoint area.

4. The apparatus of claim 1, wherein the portion of the surface has a distinct edge.

5. The apparatus of claim 1, further comprising a second light source configured for providing a second light used in generating a biometric image of the object, wherein the second light provided by the second light source has a different wavelength than that of the first light provided by the first light source.

6. The apparatus of claim 1, further comprising one or more imaging components configured for
 capturing a first image formed by the spread light in the disjoint area of the surface; and
 capturing a second image formed by an ambient light in the disjoint area of the surface, wherein the brightness measuring unit is configured for measuring the measure degree based on the first image and the second image.

7. The apparatus of claim 6, further comprising a feature extractor configured for extracting at least one feature from the first and/or the second image, wherein the at least one feature includes any of a shape, a size, or a light intensity;
 the determiner is further configured for determining whether the object is an organic body part based on the extracted at least one feature.

8. The apparatus of claim 1, wherein the brightness measuring unit is further configured for measuring variations of the measured degree when the first light source provides the first light with different wavelengths.

9. The apparatus of claim 1, wherein the brightness measuring unit is further configured for:
 measuring variations of the measured degree to which the first light is spread into the disjoint area at different points of time; and
 measuring variations of the measured degree to which the first light is spread into the disjoint area due to different pressures applied from the object to the surface.

10. The apparatus of claim 9, wherein the step of measuring variations due to the different pressures comprises at least one of the following:
 measuring an increase of ridge thickness in a brightness distribution in the disjoint area;
 measuring a change in color of ridges in the brightness distribution;
 measuring a light intensity of the ridges in the brightness distribution;
 measuring an intensity of blue component of the light in the ridges in the brightness distribution;
 measuring an intensity of green component of the light in the ridges in the brightness distribution; and
 measuring an intensity of red component of the light in the ridges in the brightness distribution.

11. The apparatus of claim 1, wherein the brightness measuring unit is further configured for measuring a light intensity of an area of the surface, which comprises a plurality of pixels.

12. The apparatus of claim 11, wherein a light intensity value at each of the plurality of pixel is determined by multiplying a first light intensity value at the pixel illuminated by the first light provided by the first light source and a second light intensity value at the pixel illuminated by a second light provided by a second light source.

13. The apparatus of claim 1, wherein the first light source is located at the opposite side of the surface on which the object is placed.

14. The apparatus of claim 1, wherein the first light provided by the first light source includes at least one of visible light, ultraviolet, infrared, white light, and laser.

15. The apparatus of claim 1, wherein rays from the first light source to the portion and rays from the portion to one or more imaging components in the apparatus, differ by an angle larger than a predetermined degree.

16. The apparatus of claim 15, wherein the predetermined degree is 45.

17. A method implemented on a device for determining whether an object is an organic body part, comprising:
   sensing presence of an object when a person places the object on a surface of the device;
   providing a first light illuminating a portion of the surface, wherein the object spreads light shone thereon to a disjoint area of the surface;
   measuring a degree to which the light is spread into the disjoint area; and
   determining whether the object is an organic body part based on the measured degree.

18. The method of claim 17, further comprising selecting one or more thresholds based on a predetermined brightness distribution caused by an organic body part spreading light shone thereon to the disjoint area, wherein the step of determining comprises comparing the measured degree with the one or more thresholds to determine whether the object is an organic body part.

19. The method of claim 18, wherein the measured degree comprises information of at least one of the following:
   a distance from the portion to a point in the disjoint area where the spread light has a certain intensity;
   a distance from a first point in the portion where the light has a peak intensity to a second point in the disjoint area where the spread light has an intensity of a certain percentage of the peak intensity;
   a distance from a first point where the light in the portion has an intensity of a first percentage of the peak intensity to a second point in the disjoint area where the spread light has an intensity of a second percentage of the peak intensity;
   a rate of light intensity change over distance from the portion to the disjoint area; and
   a light intensity computed within a predetermined region in the disjoint area.

20. The method of claim 17, wherein the portion of the surface has a distinct edge.

21. The method of claim 17, further comprising providing a second light used in forming a biometric image of the object, wherein the second light has a different wavelength than that of the first light.

22. The method of claim 17, further comprising:
   capturing a first image formed by the spread light in the disjoint area of the surface; and
   capturing a second image formed by ambient light in the disjoint area of the surface, wherein the step of measuring the degree is based on the first image and the second image.

23. The method of claim 22, further comprising extracting at least one feature from the first and/or second image, wherein
   the at least one feature includes any of a shape, a size, or a light intensity, and
   the step of determining whether the object is an organic body part is based on the at least one feature.

24. The method of claim 17, further comprising measuring variations of the measured degree when the first light has different wavelengths.

25. The method of claim 17, wherein the step of measuring further comprising:
   measuring variations of the degree to which the first light is spread into the disjoint area at different points of time; and
   measuring variations of the degree to which the first light is spread into the disjoint area due to different pressures applied from the object to the surface.

26. A system for recognizing a person, comprising:
   a surface on which an object is placed by the person;
   a light source configured for providing light illuminating a portion of the surface, wherein the object spreads the light shone on the portion to a disjoint area of the surface;
   a brightness measuring unit configured for measuring a degree to which the light is spread into the disjoint area; and
   a determiner configured for determining whether the object is an organic body part of the person based on the measured degree to generate a determination result;
   a biometric image processing unit configured for obtaining a biometric image of the object; and
   an identity determiner configured for recognizing the person based on the biometric image and the determination result.

27. An apparatus for determining an organic body part, comprising:
   a light source configured for providing light illuminating a portion of the object, wherein the object is not in contact with the apparatus, and spreads the light shone thereon to a disjoint area of the object;
   a brightness measuring unit configured for measuring a degree to which the light is spread into the disjoint area; and
   a determiner configured for determining whether the object is an organic body part based on the measured degree.

* * * * *